(12) United States Patent
Rivkees et al.

(10) Patent No.: US 11,634,498 B2
(45) Date of Patent: Apr. 25, 2023

(54) CHIMERIC ANTIGEN RECEPTORS AND USES THEREOF

(71) Applicant: University of Florida Research Foundation, Incorporated, Gainesville, FL (US)

(72) Inventors: Scott A. Rivkees, Gainesville, FL (US); Christopher Wendler, Gainesville, FL (US); Lung-Ji Chang, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 667 days.

(21) Appl. No.: 16/097,437

(22) PCT Filed: Apr. 28, 2017

(86) PCT No.: PCT/US2017/030279
§ 371 (c)(1),
(2) Date: Oct. 29, 2018

(87) PCT Pub. No.: WO2017/190096
PCT Pub. Date: Nov. 2, 2017

(65) Prior Publication Data
US 2019/0153109 A1    May 23, 2019

Related U.S. Application Data

(60) Provisional application No. 62/330,048, filed on Apr. 29, 2016.

(51) Int. Cl.
| | | |
|---|---|---|
| C07K 16/28 | (2006.01) | |
| C07K 14/725 | (2006.01) | |
| C07K 14/705 | (2006.01) | |
| C12N 5/16 | (2006.01) | |
| A61K 48/00 | (2006.01) | |
| C12N 9/64 | (2006.01) | |
| C12N 15/86 | (2006.01) | |
| A61P 35/00 | (2006.01) | |
| A61K 35/17 | (2015.01) | |

(52) U.S. Cl.
CPC .......... *C07K 16/2869* (2013.01); *A61K 35/17* (2013.01); *A61K 48/005* (2013.01); *A61P 35/00* (2018.01); *C07K 14/7051* (2013.01); *C07K 14/70521* (2013.01); *C07K 14/70596* (2013.01); *C12N 5/16* (2013.01); *C12N 9/6472* (2013.01); *C12N 15/86* (2013.01); *C12Y 304/22062* (2013.01); *C07K 2317/24* (2013.01); *C07K 2317/622* (2013.01); *C07K 2317/73* (2013.01); *C07K 2319/02* (2013.01); *C07K 2319/03* (2013.01); *C07K 2319/70* (2013.01); *C12N 2740/16043* (2013.01)

(58) Field of Classification Search
None
See application file for complete search history.

(56) References Cited

U.S. PATENT DOCUMENTS

| | | |
|---|---|---|
| 9,089,520 B2 | 7/2015 | Brenner |
| 10,117,932 B2 | 11/2018 | Shultz et al. |
| 10,647,778 B2 | 5/2020 | Chang |
| 11,041,021 B2 | 6/2021 | Chang et al. |
| 11,248,058 B2 | 2/2022 | Chang |
| 2005/0113564 A1 | 5/2005 | Campana et al. |
| 2013/0280220 A1 | 10/2013 | Ahmed et al. |
| 2014/0301993 A1 | 10/2014 | Powell, Jr. et al. |
| 2014/0322183 A1 | 10/2014 | Milone et al. |
| 2015/0023937 A1 | 1/2015 | Vera Valdes et al. |
| 2015/0118252 A1 | 4/2015 | Ho et al. |
| 2015/0329640 A1 | 11/2015 | Finer |
| 2016/0046724 A1 | 2/2016 | Brogdon et al. |
| 2016/0058857 A1* | 3/2016 | Spencer ......... A61K 39/001124 424/192.1 |
| 2017/0137515 A1 | 5/2017 | Chang et al. |
| 2017/0226216 A1 | 8/2017 | Morgan et al. |
| 2018/0022815 A1 | 1/2018 | Chang |
| 2018/0142034 A1 | 5/2018 | Chang |
| 2021/0277114 A1 | 9/2021 | Chang et al. |

FOREIGN PATENT DOCUMENTS

| | | |
|---|---|---|
| WO | WO 2012/033885 A1 | 3/2012 |
| WO | 2012/058460 * | 5/2012 |
| WO | WO 2013/074916 A1 | 5/2013 |
| WO | WO 2013/123061 A1 | 8/2013 |
| WO | WO 2013/126729 A1 | 8/2013 |

(Continued)

OTHER PUBLICATIONS

International Search Report and Written Opinion dated May 20, 2016 for Application No. PCT/US2016/017219.

(Continued)

*Primary Examiner* — Patricia Duffy
(74) *Attorney, Agent, or Firm* — Wolf, Greenfield & Sacks, P.C.

(57) ABSTRACT

Aspects of the disclosure relate to chimeric antigen receptors (CARs) comprising an antigen binding domain (e.g., anti-TSHR), transmembrane domain (e.g., CD28), and a cytoplasmic domain (e.g., CD27, CD-137, etc.) and a safety mechanism comprising an inducible apoptosis trigger. In some aspects, the disclosure relates to use of the CARs in T cells, compositions, kits and methods for the treatment of thyroid cancers.

12 Claims, 7 Drawing Sheets
Specification includes a Sequence Listing.

(56) References Cited

FOREIGN PATENT DOCUMENTS

| WO | WO 2014/039523 A1 | 3/2014 |
|---|---|---|
| WO | WO 2014/055771 A1 | 4/2014 |
| WO | WO 2014/124143 A1 | 8/2014 |
| WO | WO 2014/055657 A1 | 10/2014 |
| WO | WO 2014/165707 A2 | 10/2014 |
| WO | WO 2015/142675 A2 | 9/2015 |
| WO | WO 2015/179801 A1 | 11/2015 |
| WO | WO 2016/130598 A1 | 8/2016 |

OTHER PUBLICATIONS

International Preliminary Report on Patentability dated Aug. 24, 2017 for Application No. PCT/US2016/017219.
International Search Report and Written Opinion dated Jun. 17, 2016 for Application No. PCT/US2016/018716.
International Preliminary Report on Patentability dated Aug. 31, 2017 for Application No. PCT/US2016/018716.
International Search Report and Written Opinion dated Sep. 14, 2015 for Application No. PCT/US2015/032245.
International Preliminary Report on Patentability dated Dec. 8, 2016 for Application No. PCT/US2015/032245.
International Search Report and Written Opinion dated Sep. 6, 2017 for Application No. PCT/US2017/030279.
International Preliminary Report on Patentability dated Nov. 8, 2018 for Application No. PCT/US2017/030279.
Supplementary European Search Report dated Jun. 12, 2018 for Application No. EP 16749750.2.
Partial Supplementary European Search Report dated Jul. 27, 2018 for Application No. EP 16753166.4.
Supplementary European Search Report dated Nov. 6, 2018 for Application No. EP 16753166.4.
Callahan et al., At the bedside: CTLA-4- and PD-1-blocking antibodies in cancer immunotherapy. J Leukoc Biol. Jul. 2013;94(1):41-53. doi: 10.1189/jlb.1212631. Epub May 10, 2013.
Di Stasi et al., Inducible Apoptosis as a Safety Switch for Adopitce Cell Therapy. The New England Journal of Medicine. Nov. 3, 2011;365(18):1673-83.
Gargett et al., The inducible caspase-9 suicide gene system as a "safety switch" to limit on-target, off-tumor toxicities of chimeric antigen receptor T cells. Frontiers in Pharmacology. Oct. 2014;5:1-7.
GENBANK Submission; "AAAT18_RS09785 hypothetical protein [*Rhodococcus aetherivorans*]", Gene ID: 29568086, updated on Apr. 20, 2017. 2 pages.
GENBANK Submission; NIH/NCBI, Accession No. NP_001183.2: " TNFRSF17 TNF receptor superfamily member 17[*Homo sapiens*]", Gene ID: 608. Last updated on Sep. 30, 2018. 5 pages.
GENBANK Submission; NIH/NCBI, Accession No. NP_002988.2: "syndecan-1 precursor [*Homo sapiens*]", Nov. 5, 2002. 2 pages.
Heczey et al., Invariant NKT cells with chimeric antigen receptor provide a novel platform for safe and effective cancer immunotherapy. Blood. Oct. 30, 2014;124(18):2824-33. doi: 10.1182/blood-2013-11-541235. Epub Jul. 21, 2014.
Highfill et al., Anti-PD1 Therapy for Pediatric Sarcomas. Retrieved from the Internet. http://sarcomahelp.org/research/immuntherapy-pediatric-sarcomas.html#tpm2_1. May 10, 2016.
Lee et al., The future is now: chimeric antigen receptors as new targeted therapies for childhood cancer. Clin Cancer Res. May 15, 2012;18(10):2780-90. doi: 10.1158/1078-0432.CCR-11-1920.
Novak et al., Expression of BCMA, TACI, and BAFF-R in multiple myeloma: a mechanism for growth and survival. Blood. Jan. 2004;103(2):689-694.
Prosser et al., Tumor PD-L1 co-stimulates primary human CD8(+) cytotoxic T cells modified to express a PD1:CD28 chimeric receptor. Mol Immunol. Jul. 2012;51(3-4):263-72. doi: 10.1016/j.molimm. 2012.03.023. Epub Apr. 11, 2012.
Rappl et al., The CD3-Zeta Chimeric Antigen Receptor Overcomes TCR Hypo-Responsiveness of Human Terminal LateStage T Cells. PLoS One. 2012;7(1):e30713:1-10.
Sadelain et al., The Basic Principles of Chimeric Antigen Receptor Design. Cancer Discovery. Apr. 2013;3(4):388-98.
Sherbenou et al., The development of potential antibody-based therapies for myeloma. Blood Rev. Mar. 2015;29(2):81-91. doi: 10.1016/j.blre.2014.09.011. Epub Sep. 28, 2014.
Song et al., CD27 costimulation augments the survival and antitumor activity of redirected human T cells in vivo. Blood. Jan. 19, 2012;119(3):696-706. doi: 10.1182/blood-2011-03-344275. Epub Nov. 23, 2011.
Wu et al., The IL-15 receptor a chain cytoplasmic domain is critical for normal IL-15R α function but is not required for trans-presentation. Blood. Sep. 2008;112(12):4411-4419.
Gill et al., CAR-modified anti-CD19 T cells for the treatment of B-cell malignancies: rules of the road. Expert Opin Biol Ther. Jan. 2014;14(1):37-49. doi: 10.1517/14712598.2014.860442. Epub Nov. 21, 2013.
Straathof et al., An inducible caspase 9 safety switch for T-cell therapy. Blood. Jun. 1, 2005;105(11):4247-54. doi: 10.1182/blood-2004-11-4564. Epub Feb. 22, 2005.
U.S. Appl. No. 17/575,762, filed Jan. 14, 2022, Chang.
U.S. Appl. No. 17/321,629, filed May 17, 2021, Chang et al.

\* cited by examiner

SEQUENCE LISTING

```
<160> NUMBER OF SEQ ID NOS: 37

<210> SEQ ID NO 1
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1

Gly Gly Gly Gly Ser Gly Gly Gly Gly Ser
1               5                   10

<210> SEQ ID NO 2
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 2

Gly Gly Gly Gly Ser Gly Gly Gly Gly Ser Gly Gly Gly Gly Ser
1               5                   10                  15

<210> SEQ ID NO 3
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 3

Gly Ser Thr Ser Gly Gly Gly Ser Gly Gly Gly Ser Gly Gly Gly Gly
1               5                   10                  15

Ser Ser

<210> SEQ ID NO 4
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 4

Gly Ser Thr Ser Gly Ser Gly Lys Pro Gly Ser Ser Glu Gly Ser Thr
1               5                   10                  15

Lys Gly
```

<210> SEQ ID NO 5
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 5

Gly Gly Gly Gly Ser Gly Gly Gly
1               5

<210> SEQ ID NO 6
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 6

Val Glu Pro Lys Ser Cys Asp Lys Thr His Thr Cys Pro Pro Cys Pro
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 7

Leu Asp Pro Lys Ser Ser Asp Lys Thr His Thr Cys Pro Pro Cys Pro
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 8

Val Glu Pro Lys Ser Pro Asp Lys Thr His Thr Cys Pro Pro Cys Pro
1               5                   10                  15

<210> SEQ ID NO 9
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 9

Leu Asp Lys Thr His Thr Cys Pro Pro Cys Pro
1               5                   10

<210> SEQ ID NO 10
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 10

Gln Val Gln Leu Leu Glu Ser Gly Ala Glu Leu Val Lys Pro Gly Ala
1               5                   10                  15

Pro Val Arg Leu Ser Cys Lys Ala Ser Gly Tyr Thr Phe Thr Asn Tyr

```
            20                  25                  30
Trp Met Asn Trp Val Lys Gln Arg Pro Gly Arg Gly Leu Glu Trp Ile
             35                  40                  45

Gly Arg Ile Asp Pro Ser Asp Ser Glu Thr His Tyr Asn Gln Asn Phe
         50                  55                  60

Lys Asp Lys Ala Thr Leu Thr Val Asp Lys Ser Ser Thr Ala Tyr
 65                  70                  75                  80

Ile Gln Leu Ser Ser Leu Thr Ser Glu Asp Ser Ala Val Tyr Tyr Cys
                 85                  90                  95

Ala Arg Ser Gly Tyr Trp Gly Gln Gly Thr Thr Leu Thr Val Ser Ser
             100                 105                 110
```

<210> SEQ ID NO 11
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 11

```
Asn Tyr Trp Met Asn
1               5
```

<210> SEQ ID NO 12
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 12

```
Arg Ile Asp Pro Ser Asp Ser Glu Thr His Tyr Asn Gln Asn Phe Lys
1               5                   10                  15

Asp
```

<210> SEQ ID NO 13
<211> LENGTH: 114
<212> TYPE: PRT
<213> ORGANISM: Artificial Sequence
<220> FEATURE:
<223> OTHER INFORMATION: Synthetic Polypeptide

<400> SEQUENCE: 13

```
Glu Leu Glu Met Thr Gln Ser Pro Leu Thr Leu Ser Val Thr Thr Gly
1               5                   10                  15

Gln Pro Ala Ser Ile Ser Cys Lys Ser Ser Gln Ser Leu Leu Asp Ser
             20                  25                  30

Asp Gly Lys Thr Tyr Leu Asn Trp Leu Leu Gln Arg Pro Gly Gln Ser
         35                  40                  45

Pro Lys Arg Leu Ile Tyr Leu Val Ser Lys Val Asp Ser Gly Val Pro
     50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Trp Gln Gly
                 85                  90                  95

Thr His Ser Pro Leu Thr Phe Gly Ala Gly Thr Lys Leu Glu Leu Lys
             100                 105                 110

Arg Ala
```

```
<210> SEQ ID NO 14
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 14

Lys Ser Ser Gln Ser Leu Leu Asp Ser Asp Gly Lys Thr Tyr Leu Asn
1               5                   10                  15

<210> SEQ ID NO 15
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 15

Leu Val Ser Lys Val Asp Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 16

Trp Gln Gly Thr His Ser Pro Leu Thr
1               5

<210> SEQ ID NO 17
<211> LENGTH: 50
<212> TYPE: PRT
<213> ORGANISM: Artificial Sequence
<220> FEATURE:
<223> OTHER INFORMATION: Synthetic Polypeptide

<400> SEQUENCE: 17

Tyr Val Asn Gln Thr Asp Ile Tyr Phe Cys Lys Ile Glu Val Met Tyr
1               5                   10                  15

Pro Pro Pro Tyr Leu Asp Asn Glu Lys Ser Asn Gly Thr Ile Ile His
                20                  25                  30

Val Lys Gly Lys His Leu Cys Pro Ser Pro Leu Phe Pro Gly Pro Ser
            35                  40                  45

Lys Pro
    50

<210> SEQ ID NO 18
<211> LENGTH: 202
<212> TYPE: PRT
<213> ORGANISM: Artificial Sequence
<220> FEATURE:
<223> OTHER INFORMATION: Synthetic Polypeptide

<400> SEQUENCE: 18

Asn Lys Ile Leu Val Lys Gln Ser Pro Met Leu Val Ala Tyr Asp Asn
1               5                   10                  15

Ala Val Asn Leu Ser Cys Lys Tyr Ser Tyr Asn Leu Phe Ser Arg Glu
                20                  25                  30

Phe Arg Ala Ser Leu His Lys Gly Leu Asp Ser Ala Val Glu Val Cys
            35                  40                  45
```

```
Val Val Tyr Gly Asn Tyr Ser Gln Gln Leu Gln Val Tyr Ser Lys Thr
    50                  55                  60
Gly Phe Asn Cys Asp Gly Lys Leu Gly Asn Glu Ser Val Thr Phe Tyr
 65                  70                  75                  80
Leu Gln Asn Leu Tyr Val Asn Gln Thr Asp Ile Tyr Phe Cys Lys Ile
                 85                  90                  95
Glu Val Met Tyr Pro Pro Pro Tyr Leu Asp Asn Glu Lys Ser Asn Gly
                100                 105                 110
Thr Ile Ile His Val Lys Gly Lys His Leu Cys Pro Ser Pro Leu Phe
                115                 120                 125
Pro Gly Pro Ser Lys Pro Phe Trp Val Leu Val Val Gly Gly Val
            130                 135                 140
Leu Ala Cys Tyr Ser Leu Leu Val Thr Val Ala Phe Ile Ile Phe Trp
145                 150                 155                 160
Val Arg Ser Lys Arg Ser Arg Leu Leu His Ser Asp Tyr Met Asn Met
                165                 170                 175
Thr Pro Arg Arg Pro Gly Pro Thr Arg Lys His Tyr Gln Pro Tyr Ala
                180                 185                 190
Pro Pro Arg Asp Phe Ala Ala Tyr Arg Ser
            195                 200
```

```
<210> SEQ ID NO 19
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 19

Phe Trp Val Leu Val Val Val Gly Gly Val Leu Ala Cys Tyr Ser Leu
 1               5                  10                  15
Leu Val Thr Val Ala Phe Ile Ile Phe Trp Val
                20                  25
```

```
<210> SEQ ID NO 20
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 20

Ile Glu Val Met Tyr Pro Pro Pro Tyr Leu Asp Asn Glu Lys Ser Asn
 1               5                  10                  15
Gly Thr Ile Ile His Val Lys Gly Lys His Leu Cys Pro Ser Pro Leu
                20                  25                  30
Phe Pro Gly Pro Ser Lys Pro Phe Trp Val Leu Val Val Val Gly Gly
                35                  40                  45
Val Leu Ala Cys Tyr Ser Leu Leu Val Thr Val Ala Phe Ile Ile Phe
            50                  55                  60
Trp Val Arg Ser Lys Arg Ser Arg Leu Leu His Ser Asp Tyr Met Asn
 65                  70                  75                  80
Met Thr Pro Arg Arg Pro Gly Pro Thr Arg Lys His Tyr Gln Pro Tyr
                85                  90                  95
Ala Pro Pro Arg Asp Phe Ala Ala Tyr Arg Ser Ala Ser
                100                 105
```

```
<210> SEQ ID NO 21
```

```
<211> LENGTH: 48
<212> TYPE: PRT
<213> ORGANISM: Artificial Sequence
<220> FEATURE:
<223> OTHER INFORMATION: Synthetic Polypeptide

<400> SEQUENCE: 21

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
        35                  40                  45

<210> SEQ ID NO 22
<211> LENGTH: 39
<212> TYPE: PRT
<213> ORGANISM: Artificial Sequence
<220> FEATURE:
<223> OTHER INFORMATION: Synthetic Polypeptide

<400> SEQUENCE: 22

Lys Ser Arg Gln Thr Pro Pro Leu Ala Ser Val Glu Met Glu Ala Met
1               5                   10                  15

Glu Ala Leu Pro Val Thr Trp Gly Thr Ser Ser Arg Asp Glu Asp Leu
            20                  25                  30

Glu Asn Cys Ser His His Leu
        35

<210> SEQ ID NO 23
<211> LENGTH: 48
<212> TYPE: PRT
<213> ORGANISM: Artificial Sequence
<220> FEATURE:
<223> OTHER INFORMATION: Synthetic Polypeptide

<400> SEQUENCE: 23

Gln Arg Arg Lys Tyr Arg Ser Asn Lys Gly Glu Ser Pro Val Glu Pro
1               5                   10                  15

Ala Glu Pro Cys His Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45

<210> SEQ ID NO 24
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 24

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80
```

Arg Arg Gly Lys Gly His Asp Gly Leu Tyr Gln Gly Leu Ser Thr Ala
            85                  90                  95

Thr Lys Asp Thr Tyr Asp Ala Leu His Met Gln Ala Leu Pro Pro Arg
            100                 105                 110

<210> SEQ ID NO 25
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 25

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
            85                  90                  95

Thr Lys Asp Thr Tyr Asp Ala Leu His Met Gln Ala Leu Pro Pro Arg
            100                 105                 110

<210> SEQ ID NO 26
<211> LENGTH: 41
<212> TYPE: PRT
<213> ORGANISM: Artificial Sequence
<220> FEATURE:
<223> OTHER INFORMATION: Synthetic Polypeptide

<400> SEQUENCE: 26

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 27
<211> LENGTH: 42
<212> TYPE: PRT
<213> ORGANISM: Artificial Sequence
<220> FEATURE:
<223> OTHER INFORMATION: Synthetic Polypeptide

<400> SEQUENCE: 27

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 28
<211> LENGTH: 38

```
<212> TYPE: PRT
<213> ORGANISM: Artificial Sequence
<220> FEATURE:
<223> OTHER INFORMATION: Synthetic Polypeptide

<400> SEQUENCE: 28

Cys Trp Leu Thr Lys Lys Tyr Ser Ser Val His Asp Pro Asn
1               5                   10                  15

Gly Glu Tyr Met Phe Met Arg Ala Val Asn Thr Ala Lys Lys Ser Arg
                20                  25                  30

Leu Thr Asp Val Thr Leu
            35

<210> SEQ ID NO 29
<211> LENGTH: 42
<212> TYPE: PRT
<213> ORGANISM: Artificial Sequence
<220> FEATURE:
<223> OTHER INFORMATION: Synthetic Polypeptide

<400> SEQUENCE: 29

Ala Leu Tyr Leu Leu Arg Arg Asp Gln Arg Leu Pro Pro Asp Ala His
1               5                   10                  15

Lys Pro Pro Gly Gly Ser Phe Arg Thr Pro Ile Gln Glu Glu Gln
                20                  25                  30

Ala Asp Ala His Ser Thr Leu Ala Lys Ile
            35                  40

<210> SEQ ID NO 30
<211> LENGTH: 48
<212> TYPE: PRT
<213> ORGANISM: Artificial Sequence
<220> FEATURE:
<223> OTHER INFORMATION: Synthetic Polypeptide

<400> SEQUENCE: 30

Gln Arg Arg Lys Tyr Arg Ser Asn Lys Gly Glu Ser Pro Val Glu Pro
1               5                   10                  15

Ala Glu Pro Cys His Tyr Ser Cys Pro Arg Glu Glu Glu Gly Ser Thr
                20                  25                  30

Ile Pro Ile Gln Glu Asp Tyr Arg Lys Pro Glu Pro Ala Cys Ser Pro
            35                  40                  45

<210> SEQ ID NO 31
<211> LENGTH: 194
<212> TYPE: PRT
<213> ORGANISM: Artificial Sequence
<220> FEATURE:
<223> OTHER INFORMATION: Synthetic Polypeptide

<400> SEQUENCE: 31

Lys Arg Ile Lys Pro Ile Val Trp Pro Ser Leu Pro Asp His Lys Lys
1               5                   10                  15

Thr Leu Glu His Leu Cys Lys Lys Pro Arg Lys Asn Leu Asn Val Ser
                20                  25                  30

Phe Asn Pro Glu Ser Phe Leu Asp Cys Gln Ile His Arg Val Asp Asp
            35                  40                  45

Ile Gln Ala Arg Asp Glu Val Glu Gly Phe Leu Gln Asp Thr Phe Pro
        50                  55                  60

Gln Gln Leu Glu Glu Ser Glu Lys Gln Arg Leu Gly Gly Asp Val Gln
65                  70                  75                  80
```

```
Ser Pro Asn Cys Pro Ser Glu Asp Val Val Ile Thr Pro Glu Ser Phe
            85                  90                  95

Gly Arg Asp Ser Ser Leu Thr Cys Leu Ala Gly Asn Val Ser Ala Cys
            100                 105                 110

Asp Ala Pro Ile Leu Ser Ser Arg Ser Leu Asp Cys Arg Glu Ser
            115                 120                 125

Gly Lys Asn Gly Pro His Val Tyr Gln Asp Leu Leu Leu Ser Leu Gly
            130                 135                 140

Thr Thr Asn Ser Thr Leu Pro Pro Phe Ser Leu Gln Ser Gly Ile
145                 150                 155                 160

Leu Thr Leu Asn Pro Val Ala Gln Gly Gln Pro Ile Leu Thr Ser Leu
                165                 170                 175

Gly Ser Asn Gln Glu Glu Ala Tyr Val Thr Met Ser Ser Phe Tyr Gln
            180                 185                 190

Asn Gln

<210> SEQ ID NO 32
<211> LENGTH: 416
<212> TYPE: PRT
<213> ORGANISM: Artificial Sequence
<220> FEATURE:
<223> OTHER INFORMATION: Synthetic Polypeptide

<400> SEQUENCE: 32

Met Asp Glu Ala Asp Arg Arg Leu Leu Arg Arg Cys Arg Leu Arg Leu
1               5                   10                  15

Val Glu Glu Leu Gln Val Asp Gln Leu Trp Asp Ala Leu Leu Ser Arg
            20                  25                  30

Glu Leu Phe Arg Pro His Met Ile Glu Asp Ile Gln Arg Ala Gly Ser
            35                  40                  45

Gly Ser Arg Arg Asp Gln Ala Arg Gln Leu Ile Ile Asp Leu Glu Thr
        50                  55                  60

Arg Gly Ser Gln Ala Leu Pro Leu Phe Ile Ser Cys Leu Glu Asp Thr
65                  70                  75                  80

Gly Gln Asp Met Leu Ala Ser Phe Leu Arg Thr Asn Arg Gln Ala Ala
                85                  90                  95

Lys Leu Ser Lys Pro Thr Leu Glu Asn Leu Thr Pro Val Val Leu Arg
            100                 105                 110

Pro Glu Ile Arg Lys Pro Glu Val Leu Arg Pro Glu Thr Pro Arg Pro
            115                 120                 125

Val Asp Ile Gly Ser Gly Gly Phe Gly Asp Val Gly Ala Leu Glu Ser
            130                 135                 140

Leu Arg Gly Asn Ala Asp Leu Ala Tyr Ile Leu Ser Met Glu Pro Cys
145                 150                 155                 160

Gly His Cys Leu Ile Ile Asn Asn Val Asn Phe Cys Arg Glu Ser Gly
                165                 170                 175

Leu Arg Thr Arg Thr Gly Ser Asn Ile Asp Cys Glu Lys Leu Arg Arg
            180                 185                 190

Arg Phe Ser Ser Leu His Phe Met Val Glu Val Lys Gly Asp Leu Thr
            195                 200                 205

Ala Lys Lys Met Val Leu Ala Leu Leu Glu Leu Ala Gln Gln Asp His
            210                 215                 220

Gly Ala Leu Asp Cys Cys Val Val Val Ile Leu Ser His Gly Cys Gln
225                 230                 235                 240

Ala Ser His Leu Gln Phe Pro Gly Ala Val Tyr Gly Thr Asp Gly Cys
```

```
                        245                 250                 255
Pro Val Ser Val Glu Lys Ile Val Asn Ile Phe Asn Gly Thr Ser Cys
            260                 265                 270

Pro Ser Leu Gly Gly Lys Pro Lys Leu Phe Phe Ile Gln Ala Cys Gly
            275                 280                 285

Gly Glu Gln Lys Asp His Gly Phe Glu Val Ala Ser Thr Ser Pro Glu
            290                 295                 300

Asp Glu Ser Pro Gly Ser Asn Pro Glu Pro Asp Ala Thr Pro Phe Gln
305                 310                 315                 320

Glu Gly Leu Arg Thr Phe Asp Gln Leu Asp Ala Ile Ser Ser Leu Pro
                325                 330                 335

Thr Pro Ser Asp Ile Phe Val Ser Tyr Ser Thr Phe Pro Gly Phe Val
            340                 345                 350

Ser Trp Arg Asp Pro Lys Ser Gly Ser Trp Tyr Val Glu Thr Leu Asp
            355                 360                 365

Asp Ile Phe Glu Gln Trp Ala His Ser Glu Asp Leu Gln Ser Leu Leu
            370                 375                 380

Leu Arg Val Ala Asn Ala Val Ser Val Lys Gly Ile Tyr Lys Gln Met
385                 390                 395                 400

Pro Gly Cys Phe Asn Phe Leu Arg Lys Lys Leu Phe Phe Lys Thr Ser
                405                 410                 415

<210> SEQ ID NO 33
<211> LENGTH: 278
<212> TYPE: PRT
<213> ORGANISM: Artificial Sequence
<220> FEATURE:
<223> OTHER INFORMATION: Synthetic Polypeptide

<400> SEQUENCE: 33

Val Gly Ala Leu Glu Ser Leu Arg Gly Asn Ala Asp Leu Ala Tyr Ile
1               5                   10                  15

Leu Ser Met Glu Pro Cys Gly His Cys Leu Ile Ile Asn Asn Val Asn
            20                  25                  30

Phe Cys Arg Glu Ser Gly Leu Arg Thr Arg Thr Gly Ser Asn Ile Asp
        35                  40                  45

Cys Glu Lys Leu Arg Arg Arg Phe Ser Ser Leu His Phe Met Val Glu
50                  55                  60

Val Lys Gly Asp Leu Thr Ala Lys Lys Met Val Leu Ala Leu Leu Glu
65                  70                  75                  80

Leu Ala Gln Gln Asp His Gly Ala Leu Asp Cys Cys Val Val Val Ile
                85                  90                  95

Leu Ser His Gly Cys Gln Ala Ser His Leu Gln Phe Pro Gly Ala Val
            100                 105                 110

Tyr Gly Thr Asp Gly Cys Pro Val Ser Val Glu Lys Ile Val Asn Ile
        115                 120                 125

Phe Asn Gly Thr Ser Cys Pro Ser Leu Gly Gly Lys Pro Lys Leu Phe
130                 135                 140

Phe Ile Gln Ala Cys Gly Gly Glu Gln Lys Asp His Gly Phe Glu Val
145                 150                 155                 160

Ala Ser Thr Ser Pro Glu Asp Glu Ser Pro Gly Ser Asn Pro Glu Pro
                165                 170                 175

Asp Ala Thr Pro Phe Gln Glu Gly Leu Arg Thr Phe Asp Gln Leu Asp
            180                 185                 190

Ala Ile Ser Ser Leu Pro Thr Pro Ser Asp Ile Phe Val Ser Tyr Ser
```

```
              195                 200                 205

Thr Phe Pro Gly Phe Val Ser Trp Arg Asp Pro Lys Ser Gly Ser Trp
    210                 215                 220

Tyr Val Glu Thr Leu Asp Asp Ile Phe Glu Gln Trp Ala His Ser Glu
225                 230                 235                 240

Asp Leu Gln Ser Leu Leu Arg Val Ala Asn Ala Val Ser Val Lys
                245                 250                 255

Gly Ile Tyr Lys Gln Met Pro Gly Cys Phe Asn Phe Leu Arg Lys Lys
            260                 265                 270

Leu Phe Phe Lys Thr Ser
            275
```

<210> SEQ ID NO 34
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 34

```
Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Val Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu
            100                 105
```

<210> SEQ ID NO 35
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 35

```
Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25
```

<210> SEQ ID NO 36
<211> LENGTH: 278
<212> TYPE: PRT
<213> ORGANISM: Artificial Sequence
<220> FEATURE:
<223> OTHER INFORMATION: Synthetic Polypeptide

<400> SEQUENCE: 36

```
Val Gly Ala Leu Glu Ser Leu Arg Gly Asn Ala Asp Leu Ala Tyr Ile
1               5                   10                  15

Leu Ser Met Glu Pro Cys Gly His Cys Leu Ile Ile Asn Asn Val Asn
            20                  25                  30
```

-continued

```
Phe Cys Arg Glu Ser Gly Leu Arg Thr Arg Thr Gly Ser Asn Ile Asp
        35                  40                  45

Cys Glu Lys Leu Arg Arg Phe Ser Ser Leu His Phe Met Val Glu
    50                  55                  60

Val Lys Gly Asp Leu Thr Ala Lys Lys Met Val Leu Ala Leu Leu Glu
65                  70                  75                  80

Leu Ala Gln Gln Asp His Gly Ala Leu Asp Cys Cys Val Val Val Ile
                85                  90                  95

Leu Ser His Gly Cys Gln Ala Ser His Leu Gln Phe Pro Gly Ala Val
                100                 105                 110

Tyr Gly Thr Asp Gly Cys Pro Val Ser Val Glu Lys Ile Val Asn Ile
                115                 120                 125

Phe Asn Gly Thr Ser Cys Pro Ser Leu Gly Gly Lys Pro Lys Leu Phe
                130                 135                 140

Phe Ile Gln Ala Cys Gly Gly Glu Gln Lys Asp His Gly Phe Glu Val
145                 150                 155                 160

Ala Ser Thr Ser Pro Glu Asp Glu Ser Pro Gly Ser Asn Pro Glu Pro
                165                 170                 175

Asp Ala Thr Pro Phe Gln Glu Gly Leu Arg Thr Phe Asp Gln Leu Asp
                180                 185                 190

Ala Ile Ser Ser Leu Pro Thr Pro Ser Asp Ile Phe Val Ser Tyr Ser
                195                 200                 205

Thr Phe Pro Gly Phe Val Ser Trp Arg Asp Pro Lys Ser Gly Ser Trp
                210                 215                 220

Tyr Val Glu Thr Leu Asp Asp Ile Phe Glu Gln Trp Ala His Ser Glu
225                 230                 235                 240

Asp Leu Gln Ser Leu Leu Leu Arg Val Ala Asn Ala Val Ser Val Lys
                245                 250                 255

Gly Ile Tyr Lys Gln Met Pro Gly Cys Phe Asn Phe Leu Arg Lys Lys
                260                 265                 270

Leu Phe Phe Lys Thr Ser
        275

<210> SEQ ID NO 37
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 37

Gly Gly Gly Gly Ser
1               5
```

CHIMERIC ANTIGEN RECEPTORS AND USES THEREOF

RELATED APPLICATIONS

This Application is a national stage filing under 35 U.S.C. § 371 of international application number PCT/US2017/030279, filed Apr. 28, 2017, which claims the benefit under 35 U.S.C. § 119(e) of U.S. provisional application Ser. No. 62/330,048, filed Apr. 29, 2016, entitled "CHIMERIC ANTIGEN RECEPTORS AND USES THEREOF", the entire contents of each of which are incorporated herein by reference.

BACKGROUND

Thyroid cancers are the most common endocrine system malignancies, and are among the most rapidly increasing malignancies in children and adults. Differentiated thyroid cancers (DTC), which include papillary and follicular cancer, account for approximately 95% of thyroid cancer cases. Medullary thyroid carcinoma (MTC) accounts for about 5% of thyroid cancers. Most forms of DTC are treatable in the form of surgery and radioactive iodine-131 ($^{131}$I). Yet, some forms of DTC are unresponsive to $^{131}$I. Thus, novel forms of therapy for DTC are needed.

SUMMARY

In some aspects, the disclosure relates to chimeric antigen receptors (CARs) comprising an antigen binding domain (e.g., anti-TSHR binding domain, anti-sodium-iodide (Na/I) symporter (NIS) binding domain, anti-thyroglobulin (TG) binding domain, etc.), and/or a cytoplasmic domain of a interleukin(IL)-15-receptor α, and/or a chimeric cytoplasmic domain including a CD27 cytoplasmic domain fused to a 4-1BB cytoplasmic domain. Use of the CARs in T cells, compositions, kits and methods is also contemplated by the disclosure.

Aspects of the disclosure relate to CARs comprising a cytoplasmic domain of a interleukin(IL)-15-receptor α, and uses of such CARs to produce CAR T-cells (CARTs) and/or CAR-modified immune cells such as NK (natural killer) cells, which can be used in various methods, such as treatment methods, or compositions.

The disclosure relates, in part, to the discovery that including the cytoplasmic domain of IL-15-receptor α (IL-15Rα) in a CAR construct resulted in CARTs with greater expansion potential upon antigen stimulation and higher killing efficacy. Further, in some embodiments, the CARTs maintained killing efficacy even on repetitive addition of an excess of target cells. In some embodiments, the CARTs also produced increased amounts of effector cytokines, as determined by intracellular staining and flow cytometry based bead assays.

Accordingly, aspects of the disclosure relate to a chimeric antigen receptor (CAR) comprising an antigen binding domain; a transmembrane domain; and a cytoplasmic domain containing an interleukin 15-receptor α (IL-15Rα) cytoplasmic domain. In some embodiments, the transmembrane domain is a CD28 or CD8 transmembrane domain. In some embodiments, the cytoplasmic domain further comprises a CD3zeta signal transduction domain. In some embodiments, the cytoplasmic domain further comprises a CD27 signaling domain. In some embodiments, the antigen binding domain is a single-chain variable fragment (scFv). In some embodiments, the antigen binding domain is specific for thyroid specific hormone receptor (TSHR). In some embodiments, the antigen binding domain is anti-TSHR scFv.

Aspects of the disclosure relate to CARs comprising a chimeric cytoplasmic domain including a CD27 cytoplasmic domain fused to a 4-1BB cytoplasmic domain, and uses of such CARs to produce CARTs and/or CAR-modified immune cells such as NK (natural killer) cells, which can be used in various methods, such as treatment methods, or compositions.

In some aspects, the disclosure relates to a chimeric antigen receptor (CAR) comprising: an antigen binding domain; a transmembrane domain; and a cytoplasmic domain containing a CD27 intracellular domain.

In some embodiments, the transmembrane domain is a CD28 or CD8 transmembrane domain. In some embodiments, the cytoplasmic domain further comprises a 4-1BB intracellular domain. In some embodiments, the cytoplasmic domain further comprises a CD3zeta signal transduction domain. In some embodiments, the cytoplasmic domain further comprises an iCasp9 domain and/or a FK506 binding protein (FKBP) domain. In some embodiments, the antigen binding domain is a single-chain variable fragment (scFv).

In some embodiments, a CAR comprises a CD28 transmembrane domain, cytoplasmic domain comprising a CD27 intracellular domain and a 4-1BB intracellular domain, and a CD3zeta signal transduction domain. In some embodiments, a CAR further comprises an iCasp9 domain and/or a FKBP domain.

In some embodiments, a CAR further comprises a first spacer between the CD28 transmembrane domain and the cytoplasmic domain comprising a CD27 intracellular domain and a 4-1BB intracellular domain, and a second spacer between the cytoplasmic domain comprising a CD27 intracellular domain and a 4-1BB intracellular domain and the CD3zeta signal transduction domain. In some embodiments, the CAR further comprises a third spacer between the CD3zeta signal transduction domain and the iCasp9 domain and/or a FKBP domain. In some embodiments, the antigen binding domain of a CAR is specific for CD30.

Aspects of the disclosure relate to CARs (e.g., a 4S-CAR) targeting cellular markers of thyroid cancers which, when engineered into immune cells (for example T-cells) enables the targeted killing of thyroid cancer cells (e.g., DTC cells), thus providing a means to treat thyroid cancers. Aspects of the disclosure relate to CARs comprising an antigen-binding domain specific for thyroid-specific hormone receptor (TSHR), and uses of such CARs to produce CAR-modified immune cells such as T cells (also referred to herein as CARTs) or NK (natural killer) cells, which can be used in various methods, such as treatment methods, or compositions. In some aspects of the disclosure, such CARs are used to treat differentiated thyroid cancers, including papillary thyroid cancer or follicular thyroid cancer, in a subject, such as a subject having thyroid cancer refractory to $^{131}$I and/or surgery, or such as a subject where the treating clinician wishes to avoid the risk of surgery or the risk of administering $^{131}$I.

As described by the disclosure, it was found that TSHR-specific CAR-expressing T cells could kill both papillary thyroid cancer or follicular thyroid cancer, cells, both of which express TSHR. As a result, it is expected that TSHR-specific CARs will be useful for treatment of differentiated thyroid cancers, including both papillary thyroid cancer or follicular thyroid cancer, and perhaps more generally thyroid cancers. It should be appreciated that T cells expressing CARs that bind specifically to other thyroid cancer-specific antigens (e.g., sodium-iodide (Na/I) symporter (NIS), thyroglobulin (TG), etc.) are also contemplated by the disclosure.

Aspects of the disclosure relate to a chimeric antigen receptor (CAR) comprising an antigen binding domain specific for TSHR; a transmembrane domain; and a cytoplasmic domain containing one or more (e.g., one, two, or three) of a CD27 signaling domain, a 4-1BB intracellular domain, and a CD3zeta signal transduction domain. In some embodiments, the transmembrane domain is a CD28 or CD8 transmembrane domain. In some embodiments, the antigen binding domain is a single-chain variable fragment (scFv).

Other aspects of the disclosure relate to a nucleic acid comprising a sequence that encodes the CAR of any one of the above embodiments or as otherwise described herein.

Yet other aspects relate to an immune cell comprising a CAR of any one of the above embodiments or as otherwise described herein and/or a nucleic acid of any one of the above embodiments or as otherwise described herein. In some embodiments, the immune cell is a T cell or NK cell. In some embodiments, the immune cell is a T cell.

Other aspects of the disclosure relate to a composition comprising a plurality of the immune cell of any one of the above embodiments or as otherwise described herein. In some embodiments, the composition comprises a pharmaceutically acceptable carrier.

Another aspect of the disclosure relates to a method of generating a plurality of CAR-modified immune cells, the method comprising introducing a lentiviral vector comprising a nucleic acid of any one of the above embodiments or as otherwise described herein into a plurality of immune cells. In some embodiments, the immune cells are T cells.

Other aspects of the disclosure relate to a method of treating a subject having a disease, the method comprising administering an immune cell of any one of the above embodiments or as otherwise described herein, the composition of any one of the above embodiments or as otherwise described herein, or the plurality of immune cells produced by a method of any one of the above embodiments or as otherwise described herein into a subject having a disease or at risk of having a disease.

In some embodiments, the immune cell is a T cell. In some embodiments, the immune cell is a plurality of immune cells in a composition.

In some embodiments, the disease is thyroid cancer. In some embodiments, the disease is a differentiated thyroid cancer (e.g., papillary cancers or follicular cancers). In some embodiments, the disease is a differentiated thyroid cancer refractory to conventional therapies (e.g., surgery and/or treatment with $^{131}$I).

In further embodiments, the CAR is constructed with a single chain fragment variable (scFv) domain that targets TSHR. In some embodiments, TSHR binding domain (e.g., anti-TSHR scFv) can be derived from an anti-TSHR monoclonal (for example, the mouse monoclonal antibody clone 3BD10, as described by Chazenbalk et al., *J Clin Endocrinol Metab*, 84:702-710 (1999) and Chen et al., *Mol Endocrinol.* 29:99-107 (2015)). In some embodiments, the sequence derived from the anti-TSHR monoclonal antibody is humanized prior to incorporation as the scFv element in the CAR.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It should be appreciated that in greyscale versions of the drawings, GFP fluorescence appears as areas of shading (e.g., white shading or grey shading).

DETAILED DESCRIPTION

Figure 1:
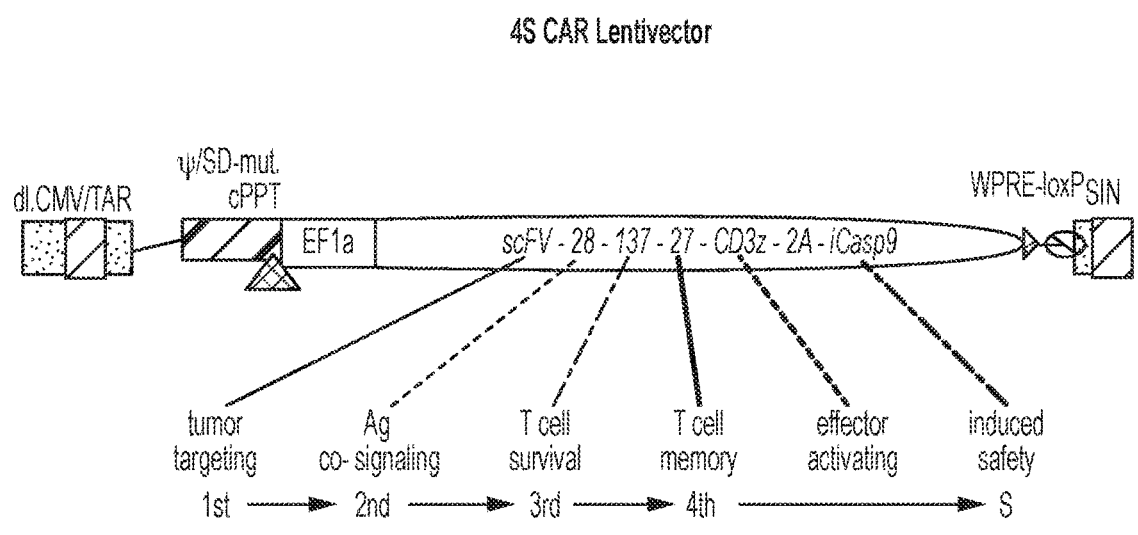
FIG. 1 shows a schematic map of a CAR vector as described by the disclosure.

In some aspects, the disclosure relates to chimeric antigen receptors (CARs) comprising an antigen binding domain (e.g., anti-TSHR, anti-sodium-iodide (Na/I) symporter (NIS), anti-thyroglobulin (TG), etc.), and/or a cytoplasmic domain of a interleukin(IL)-15-receptor a, and/or a chimeric cytoplasmic domain including a CD27 cytoplasmic domain fused to a 4-1BB cytoplasmic domain. Use of the CARs in T cells, compositions, kits and methods is also contemplated by the disclosure.

The disclosure relates, in some embodiments, to chimeric antigen receptors (CARs) and uses thereof in T cells (e.g., to make CAR T cells), methods, nucleic acids, compositions, kits and the like. CARs are molecules that combine antibody-based specificity for a desired antigen (e.g., tumor antigen) with a T cell receptor-activating intracellular domain to generate a chimeric protein that exhibits a specific anti-tumor cellular immune activity. It should be appreciated that, in some embodiments, non-limiting examples of arrangements of CARs are described from left to right, N-terminus to C-terminus of the CAR.

In some aspects, the disclosure relates to CARs having an interleukin 15-receptor α (IL-15Rα) cytoplasmic domain. CARs containing this domain had several advantageous and surprising features including greater expansion potential upon antigen stimulation, higher killing efficacy, maintained killing efficacy upon repetitive addition of excess target cells, and an increased amount of effector cytokines compared to CARs not containing this domain.

In some embodiments, the disclosure relates, in part, to the use of T cells genetically modified to stably express a desired CAR, e.g., containing a IL-15Rα cytoplasmic domain, containing a TSHR antigen binding domain, and/or containing another antigen characteristic of DTC cells (e.g., NIS, TG, etc.). T cells expressing a CAR are referred to herein as CAR T cells, CARTs, or CAR modified T cells. Preferably, the cell can be genetically modified to stably express an antibody binding domain on its surface, conferring novel antigen specificity that is MHC independent. In some instances, the T cell is genetically modified to stably express a CAR that combines an antigen recognition domain of a specific antibody with an transmembrane domain and a cytoplasmic domain into a single chimeric protein. In some embodiments, two CAR proteins dimerize (e.g., form homo- or heterodimers) in vivo.

In some embodiments, a CAR comprises an antigen binding domain, a transmembrane domain, a cytoplasmic domain comprising an IL-15Rα cytoplasmic domain, optionally further comprising a CD3 zeta (CD3z) signaling domain and/or a CD27 signaling domain. In some embodiments, the arrangement of the elements of the CAR is selected from one of the following non-limiting examples of arrangements (from N-terminus to C-terminus):

scFv-CD28-IL-15Rα-CD3z
scFv-CD28-CD27-IL-15Rα-CD3z
scFv-CD28-(4-1BB)-CD27-IL-15Rα-CD3z
scFv-CD8-CD27-IL-15Rα-CD3z
scFv-CD8-(4-1BB)-CD27-IL-15Rα-CD3z

In some aspects, the disclosure relates to CARs having a TSHR antigen binding domain and an intracellular domain comprising a 4-1BB intracellular domain and a CD27 intracellular domain. In some embodiments, the CARs further comprise a self-destructive domain (e.g., an iCasp9-FKBP domain) that further improves safety. CARs containing these domains had several surprising features including an acceptable safety profile, and mediate effective killing of TSHR cancer cells.

In some embodiments, a CAR (e.g., CAR having a TSHR binding domain) comprises an antigen binding domain, a transmembrane domain, a cytoplasmic domain comprising a 4-1BB intracellular domain and a CD27 intracellular domain, optionally further comprising a CD3 zeta (CD3z) signaling domain, and/or an apoptosis-inducing iCasp9-FKBP domain. In some embodiments, the arrangement of the elements of the CAR is selected from one of the following non-limiting examples of arrangements (from N-terminus to C-terminus):

scFv-CD28-(4-1BB)-CD27-CD3z-iCasp9-FKBP
scFv-CD28-CD27-(4-1BB)-CD3z-iCasp9-FKBP
scFv-CD8-(4-1BB)-CD27-CD3z-iCasp9-FKBP
scFv-CD8-CD27-(4-1BB)-CD3z-iCasp9-FKBP
scFv-CD28-CD137-CD27-CD3z-2A-iCasp9

In some aspects, the disclosure relates to the discovery that TSHR was expressed on both papillary and follicular cancers cells and that TSHR-specific CAR-expressing T cells could kill both papillary and follicular cancers cells. As a result, it is expected that such CARs (e.g., TSHR-specific CARs) will be useful for treatment of DTCs, particularly papillary and follicular cancers of the thyroid. In some embodiments, TSHR-specific CARs contain an antigen binding domain (such as an scFv) specific for TSHR. In some embodiments, the arrangement of the elements of the CAR (e.g., TSHR-specific CAR) is selected from one of the following non-limiting examples of arrangements (from N-terminus to C-terminus):

TSHRscFv-CD28-(4-1BB)-CD27-CD3z
TSHRscFv-CD8-CD28-CD3z
TSHRscFv-CD28-(4-1BB)-CD27-CD3z-Casp9-FKBP
TSHRscFv-CD8-CD28-CD3z-Casp9-FKBP
TSHRscFv-CD28-CD137-CD27-CD3z-2A-iCasp9

In some embodiments, a CAR molecule includes several hinge elements and/or spacer sequences (such as between individual domain elements). In some embodiments, the spacer and/or hinge sequences of the CAR are selected from one or more of the following examples of sequences: GGGGS (SEQ ID NO: 37), GGGGSGGGGS (SEQ ID NO: 1), (GGGGS)×3 (SEQ ID NO: 2), GST-SGGGSGGGSGGGGSS (SEQ ID NO: 3), GST-SGSGKPGSSEGSTKG (SEQ ID NO: 4), GGGGSGGG (SEQ ID NO: 5), VEPKSCDKTHTCPPCP (SEQ ID NO: 6), LDPKSSDKTHTCPPCP (SEQ ID NO: 7), VEPKSPDKTH-TCPPCP (SEQ ID NO: 8), or LDKTHTCPPCP (SEQ ID NO: 9).

In some embodiments, one or more of the spacer and/or hinge sequences of the CAR is a 2A peptide linker, for example FMDV 2A (F2A); equine rhinitis A virus (ERAV) 2A (E2A); porcine teschovirus-1 2A (P2A) and Thoseaasigna virus 2A (T2A), and porcine teschovirus-1 2A (P2A), for example as disclosed by Kim et al., *PLoS ONE* 6(4): e18556 (2011).

In some embodiments, the disclosure relates, in part, to a CAR that incorporates a series of domains that provide different functional aspects that may synergistically work together to improve efficacy. For example, the CAR may include one or more of: an antigen binding domain, a hinge domain, an antigen co-signaling domain that stimulates activity (e.g., an IL-15Rα cytoplasmic domain, a 4-1BB cytoplasmic domain, a CD28 cytoplasmic domain, or another cytoplasmic domain), a survival domain that increases T-cell or immune effector cell survival (e.g., a CD137 domain), a T-cell or immune effector cell memory domain (e.g., CD27), and an effector activating domain (e.g., CD3z). Alternatively, the CAR may further include a domain that provides safety (e.g., an apoptosis-inducing domain such as iCasp9 or iCasp9-FKBP).

In some embodiments, a CAR comprises an extracellular domain having an antigen binding domain, a transmembrane domain, and a multi-functional cytoplasmic domain. In some embodiments, the CAR comprises a fully human antibody or antibody fragment. In some embodiments, the transmembrane domain that naturally is associated with one of the domains in the CAR is used. In another embodiment, the transmembrane domain can be selected or modified by amino acid substitution to avoid binding of such domains to the transmembrane domains of the same or different surface membrane proteins to minimize interactions with other members of the receptor complex.

In some embodiments, the CAR T cells or other CAR-modified immune cells (e.g., CAR-modified NK cells) are generated by introducing a lentiviral vector comprising a nucleic acid that encodes a desired CAR into T cells or other immune cells (e.g., into NK cells). In some embodiments, the lentiviral vector comprises a nucleic acid that encodes a CAR comprising an antigen binding domain (e.g., that targets CD19), a transmembrane domain, and a cytoplasmic domain. In some embodiments, the CAR T cells or other CAR-modified immune cells (e.g., NK cells) are able to replicate in vivo resulting in long-term persistence that can lead to sustained tumor control. In some embodiments, the CAR T cell or other CAR-modified immune cells can be generated by transfecting a transposon or RNA encoding the desired CAR, into the T cells or other immune cells. In some embodiments, the CAR is transiently expressed in the genetically modified CAR T cell or other CAR-modified immune cells.

In some embodiments, the disclosure relates to administering a genetically modified immune cell (e.g., a genetically modified T cell or NK cell) expressing a CAR for the treatment of a patient having cancer or at risk of having cancer, or having an autoimmune disease or at risk of having an autoimmune disease, e.g., using lymphocyte infusion. In some embodiments, autologous lymphocyte infusion is used in the treatment. In some embodiments, autologous PBMCs are collected from a patient in need of treatment and immune cells (e.g., T cells or NK cells) are activated and expanded using the methods described herein and known in the art and then infused back into the patient.

In further embodiments, cell surface antigens that are selectively expressed on thyroid cells and DTC are identified for targeting by CAR. These include the thyroid stimulating hormone receptor (TSHR), a G protein-coupled receptor with a large and antigenic carboxyl moiety. In some embodiments, an anti-TSHR antibody is used as a source of complementarity determining regions (CDRs) for use in a CAR. In some embodiments, the anti-TSHR antibody is the murine antibody 3BD10. In some embodiments, the antibody comprises a heavy chain variable region with an amino acid sequence comprising:

(SEQ ID NO: 10)
QVQLLESGAELVKPGAPVRLSCKASGYTFTNYWMNWVKQRPGRGLEWI

GRIDPSDSETHYNQNFKDKATLTVDKSSSTAYIQLSSLTSEDSAVYYC

ARSGYWGQGTTLTVSS.

In some embodiments, the antibody comprises a CDRH1 having an amino acid sequence comprising NYWMN (SEQ ID NO: 11), a CDRH2 having an amino acid sequence comprising RIDPSDSETHYNQNFKD (SEQ ID NO: 12), and a CDRH3 having an amino acid sequence comprising SGY. In some embodiments, the antibody comprises a light chain variable region having an amino acid sequence comprising:

(SEQ ID NO: 13)
ELEMTQSPLTLSVTTGQPASISCKSSQSLLDSDGKTYLNWLLQRPGQS

PKRLIYLVSKVDSGVPDRFTGSGSGTDFTLKISRVEAEDLGVYYCWQG

THSPLTFGAGTKLELKRA.

In some embodiments, the antibody comprises a CDRL1 having an amino acid sequence comprising KSSQSLL-DSDGKTYLN (SEQ ID NO: 14), a CDRL2 having an amino acid sequence comprising LVSKVDS (SEQ ID NO: 15), and a CDRL3 having an amino acid sequence comprising WQGTHSPLT (SEQ ID NO: 16).

In some embodiments such amino acid sequences can be expressed in a CAR that targets TSHR, and thus a CAR-T cell that can target thyroid cancer cells. In other embodiments the CDRs of the antibody can be expressed in the scFv domain of a CAR that comprises fully human sequence, sequence consistent with human antibody library sequences, or humanized sequences so that immunogenicity in human subject of the CAR itself is minimized. In some embodiments the nucleic acids coding for such amino acid sequences or the CDRs from such sequences embedded in human or humanized backgrounds can be codon optimized for expression in humans prior to insertion into the CAR gene cassette.

Although TSHRs are highly expressed in the thyroid, TSHR protein has been detected in other tissues at lower levels, such as the brain, with some antibodies, according to the Human Protein Atlas (HPA) database (proteinatlas.org/). Therefore, some aspects of the disclosure relate to other thyroid specific antigens for the production of CARs (e.g., CARs or CARTs for the useful treatment of thyroid cancers). For example, one thyroid cell surface antigen that can be targeted is the sodium-iodide (Na/I) symporter (NIS), also known as Solute carrier family 5 (sodium/iodide cotransporter), member 5 (SLC5A5). The NIS is highly expressed in the thyroid, with some expression in the stomach and salivary gland according to HPA. In another example, thyroglobulin (TG) is highly specific to the thyroid gland. Although TG is a secreted protein, it is also expressed, in some embodiments, on the surface of thyroid epithelial cells. TG expression has not been detected in any other human tissues. In some embodiments, monoclonal antibodies against these proteins (e.g., NIS, TG, etc.) can be used following the methods described herein, and methods known in the art, to design further anti-thyroid CARs.

Definitions

Unless defined otherwise, all technical and scientific terms used herein have the same meaning as commonly understood by one of ordinary skill in the art to which the disclosure pertains.

"Activation", as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies of the disclosure may exist in a variety of forms including, for example, polyclonal antibodies, monoclonal antibodies, Fv, Fab and F(ab)$_2$, as well as single chain antibodies, human antibodies, and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations, κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present disclosure includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "tumor antigen" as used herein refers to an antigen associated with a cancer cell. In some embodiments, the tumor antigen is THSR, which is typically associated with DTCs (e.g., papillary thyroid cancer, follicular thyroid cancer, etc. Examples of other tumor antigens include, but are not limited to, CD2, CD5, CD10, CD20, CD22, CD30, CD33, CD38, CD52, CD56, CD74, CD138, CD317, Her2, VEGFR2, EGFRviii, CXCR4, BCMA, GD2, GD3, and any other antigens over-expressed in tumor cells.

In some embodiments the tumor antigen is Thyrotropin Receptor, also known as Thyroid Stimulating Hormone Receptor (TSHR). A non-limiting example of a TSHR sequence is documented as GenBank: AAI56780.1.

The term "target antigen" as used herein refers to an antigen associated with a disease-associated target cell. Examples of target antigens include but are not limited to TSHR, CD2, CD5, CD7, CD10, CD19, CD20, CD22, CD30, CD33, CD38, CD52, CD56, CD74, CD138, CD317, Her2, VEGFR2, EGFRviii, CXCR4, BCMA, GD2, GD3, and any other antigens over-expressed in target cells or diseased cells The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the disclosure in prevention of the occurrence of tumor in the first place.

As used herein, the term "autologous" is meant to refer to any material derived from the same individual to which it is later to be re-introduced into the individual.

"Allogeneic" refers to a graft derived from a different animal of the same species. "Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include, but are not limited to, thyroid cancer, breast cancer, prostate cancer, ovarian cancer, cervical cancer, skin cancer, pancreatic cancer, colorectal cancer, renal cancer, liver cancer, brain cancer, lymphoma, leukemia (e.g., chronic lymphocytic leukemia, acute lymphoblastic leukemia, pediatric acute B cell leukemia, or post hematopoietic stem cell transplant relapsed leukemia), lung cancer and the like. In some embodiments, cancer refers to B-cell related malignancies (e.g., B-cell chronic lymphocytic leukemia, acute lymphoblastic leukemia, B-cell prolymphocytic leukemia, precursor B lymphoblastic leukemia, Hairy cell leukemia, diffuse large B cell lymphoma, follicular lymphoma, marginal zone lymphoma, small cell lymphocytic lymphoma, mantle cell lymphoma, Burkitt lymphoma, primary mediastinal (thymic) large B-cell lymphoma, lymphoplasmacytic lymphoma, nodal marginal zone B cell lymphoma, intravascular large B-cell lymphoma, primary effusion lymphoma, lymphomatoid granulomatosis, or plasmablastic lymphoma).

In some embodiments, cancer refers to thyroid cancers (e.g., papillary thyroid cancer, follicular thyroid cancer etc.). Thyroid cancers are the most common endocrine system malignancies, and are among the most rapidly increasing malignancies in children and adults. Differentiated thyroid cancers (DTC), which include papillary and follicular cancer, account for approximately 95% of thyroid cancer cases. Medullary thyroid carcinoma (MTC) accounts for about 5% of thyroid cancers. Most forms of DTC are treatable in the form of surgery and radioactive iodine ($^{131}$I). Yet, some forms of DTC are unresponsive to $^{131}$I, and the use of radioactive iodine in thyroid cancer carries serious risks that has called into question the safety of $^{131}$I therapy.

The term "autoimmune disease" as used herein refers to a disease characterized by an abnormal immune response of the body against the body's own cells and tissues. The immune response may be systemic or may be restricted to certain tissue types or organs. Examples of various autoimmune diseases include, but are not limited to, acute disseminated encephalomyelitis, Addison's disease, alopecia areata, autoimmune cardiomyopathy, autoimmune hemolytic anemia, autoimmune hepatitis, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticarial, autoimmune uveitis, Behçet's disease, Celiac disease, Churg-Strauss syndrome, cold agglutinin disease, Crohn's disease, dermatomyositis, diabetes mellitus type 1, eosinophilic fasciitis, gastrointestinal pemphigoid, Goodpasture's syndrome, Graves' disease, Guillain-Barré syndrome, Hashimoto's encephalopathy, Hashimoto's thyroiditis, idiopathic thrombocytopenic purpura, lupus erythematosus, Miller-Fisher syndrome, mixed connective tissue disease, multiple sclerosis, myasthenia gravis, pemphigus vulgaris, pernicious anaemia, polymyositis, primary biliary cirrhosis, psoriasis, psoriatic arthritis, relapsing polychondritis, rheumatoid arthritis, rheumatic fever, Sjögren's syndrome, temporal arteritis, transverse myelitis, ulcerative colitis, undifferentiated connective tissue disease, vasculitis, and Wegener's granulomatosis.

The term "infection" as used herein refers to an invasion of a host's cells or tissues with an infectious organism, such as a bacteria, virus, or fungus.

An "effective amount" as used herein, means an amount which provides a therapeutic or prophylactic benefit.

As used herein, the term "exogenous" refers to any material introduced from or produced outside an organism, cell, tissue or system.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

Unless otherwise specified, a "nucleotide sequence or nucleic acid encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. *Lenti* viruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of *lenti* viruses. Vectors derived from *lenti* viruses offer the means to achieve significant levels of gene transfer in vivo.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

"Codon-optimized" means that codons relating to a specific amino acid are optimized for translational efficiency of a gene of interest. Codon optimization typically involves evaluating the gene or sequence of interest and substituting the codon with a more prevalent or common codon used for the same amino acid in a specific cell or species. Programs used by those in the art to evaluate codon optimization include those provided by Integrated DNA Technologies, EnCor Biotechnology, Inc., JCat, OptimumGene™ (GenScript USA, Inc., Pisataway, N.J. 08854), etc. The sequences encoding the CAR embodiments described herein may be codon-optimized, which can increase their translational efficiency.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" or "overexpression" is intended to indicate an abnormal level of expression (e.g., of the tumor antigen) in a cell from a disease area (e.g., a solid tumor within a specific tissue or organ of the patient) relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In some embodiments, the patient, subject or individual is a human. In some embodiments, the patient, subject or individual is a child (such as 18 years of age or younger).

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner. A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

By the term "specifically binds" or "specific for", as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "subject" is intended to include living organisms in which an immune response can be elicited (e.g., mammals). Examples of subjects include humans, dogs, cats, mice, rats, and transgenic species thereof.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Compositions

In some embodiments, the disclosure provides a chimeric antigen receptor (CAR) comprising (a) an extracellular domain comprising an antigen binding domain, (b) a transmembrane domain and (c) a cytoplasmic domain. It should be appreciated that in some embodiments, CAR molecules described by the following non-limiting examples of arrangements are from left to right, N-terminus to C-terminus of the CAR. A CAR molecule as described by the disclosure may comprise or further comprise any other combination of elements as described herein.

In some embodiments, a CAR as described by the disclosure is fully human

In some embodiments, a CAR has a cytoplasmic domain comprising, a CD27 cytoplasmic domain in combination with one or more other cytoplasmic domains described herein, e.g., a 4-1BB intracellular domain and/or a CD3 zeta domain. In some embodiments, the cytoplasmic domain further comprises a safety-enhancing domain, e.g., an apoptosis-inducing iCasp9-FKBP domain. In some embodiments, the arrangement of the elements of a CAR is selected from one of the following non-limiting examples of arrangements:

scFv-CD28-(4-1BB)-CD27-CD3z-iCasp9-FKBP
scFv-CD28-CD27-(4-1BB)-CD3z-iCasp9-FKBP
scFv-CD8-(4-1BB)-CD27-CD3z-iCasp9-FKBP
scFv-CD8-CD27-(4-1BB)-CD3z-iCasp9-FKBP
scFv-CD28-CD137-CD27-CD3z-2A-iCasp9

In some embodiments, a CAR described by the disclosure comprises an antigen binding domain specific for TSHR. In some embodiments, the arrangement of the elements of the CAR is selected from one of the following non-limiting examples of arrangements:

TSHRscFv-CD28-(4-1BB)-CD27-CD3z
TSHRscFv-CD8-CD28-CD3z
TSHRscFv-CD28-(4-1BB)-CD27-CD3z-Casp9-FKBP
TSHRscFv-CD8-CD28-CD3z-Casp9-FKBP
TSHRscFv-CD28-CD137-CD27-CD3z-2A-iCasp9

Between the extracellular domain (comprising the antigen binding domain) and the transmembrane domain of the CAR, or between the cytoplasmic domain and the transmembrane domain of the CAR, there may be incorporated a spacer or hinge domain. As used herein, the term "spacer domain" generally means any oligo- or polypeptide that functions to link the transmembrane domain to the extracellular domain and/or the cytoplasmic domain in the polypeptide chain. As used herein, a hinge domain generally means any oligo- or polypeptide that functions to provide flexibility to the CAR, or domains thereof, and/or prevent steric hindrance of the CAR, or domains thereof. In some embodiments, a spacer or hinge domain may comprise up to 300 amino acids, preferably 10 to 100 amino acids and most preferably 5 to 20 amino acids. It also should be appreciated that one or more spacer domains may be included in other regions of a CAR, as aspects of the disclosure are not limited in this respect.

It is to be understood that a CAR can include a region (e.g., an antigen binding domain, a transmembrane domain, a cytoplasmic domain, a signaling domain, a safety domain, and/or a linker, or any combination thereof) having a sequence provided herein or a variant thereof or a fragment of either one thereof (e.g., a variant and/or fragment that retains the function required for the CAR activity) can be included in a CAR protein as described herein. In some embodiments, a variant has 1, 2, 3, 4, 5, 6, 7, 8, 9, or 10 amino acid changes relative to the illustrated sequence. In some embodiments, a variant has a sequence that is at least 80%, at least 85%, at least 90%, 90%-95%, at least 95% or at least 99% identical to the illustrated sequence. In some embodiments, a fragment is 1-5, 5-10, 10-20, 20-30, 30-40, or 40-50 amino acids shorter than a sequence provided herein. In some embodiments, a fragment is shorter at the N-terminal, C-terminal, or both terminal regions of the sequence provided. In some embodiments, a fragment contains 80%-85%, 85%-90%, 90%-95%, or 95%-99% of the number of amino acids in a sequence provided herein.

In some embodiments, the spacer and/or hinge sequences of the CAR are selected from one or more of the following examples of sequences:

```
Spacer Sequences:
                                        (SEQ ID NO: 37)
GGGGS (SEQ ID NO: 1)
GGGGSGGGGS (SEQ ID NO: 2)
GGGGS x3

GS18:
                                        (SEQ ID NO: 3)
GSTSGGGSGGGSGGGGSS

218S:
                                        (SEQ ID NO: 4)
GSTSGSGKPGSSEGSTKG

GS8:
                                        (SEQ ID NO: 5)
GGGGSGGG

Hinge Sequences:
Native:
                                        (SEQ ID NO: 6)
VEPKSCDKTHTCPPCP

C233S:
                                        (SEQ ID NO: 7)
LDPKSSDKTHTCPPCP

C233P:
                                        (SEQ ID NO: 8)
VEPKSPDKTHTCPPCP

Delta5:
 (SEQ ID NO: 9)
LDKTHTCPPCP
```

Antigen Binding Domains

In some embodiments, a CAR as described by the disclosure comprises an antigen binding domain. The choice of binding domain depends upon the type and number of ligands that define the surface of a target cell. For example, the antigen binding domain may be chosen to recognize a ligand that acts as a cell surface marker on target cells associated with a particular disease state, such as cancer or an autoimmune disease. Thus examples of cell surface markers that may act as ligands for the antigen binding domain in a CAR of the disclosure include those associated with cancer cells and other forms of diseased cells, for example, autoimmune disease cells and pathogen infected cells. In some embodiments, a CAR of the disclosure is engineered to target a tumor antigen of interest by way of engineering a desired antigen binding domain that specifically binds to an antigen on a tumor cell. In the context of the present disclosure, "tumor antigen" refers to antigens that are common to specific hyperproliferative disorders such as cancer. The antigens discussed herein are merely included by way of example. The list is not intended to be exclusive and further examples will be readily apparent to those of skill in the art.

The antigen binding domain of the CAR may target, for example, TSHR, NIS, TG, CD19, CD30, or GD2. Other examples of target antigens include, but are not limited, to CD2, CD5, CD7, CD10, CD19, CD20, CD22, CD30, CD33, CD38, CD52, CD56, CD74, CD138, CD317, Her2, VEGFR2, EGFRviii, CXCR4, BCMA, GD2, GD3, and any other antigens over-expressed in target or diseased cells. Other antigens specific for cancer that may be targeted at taught in PCT publication No. WO2013/123061 (page 20), which is incorporated herein by reference with respect to the antigens recited therein.

The antigen binding domain can be any domain that binds to the antigen including but not limited to monoclonal antibodies, scFvs, polyclonal antibodies, synthetic antibodies, human antibodies, humanized antibodies, and fragments thereof. In some instances, it is beneficial for the antigen binding domain to be derived from the same species in which the CAR will ultimately be used in. For example, for use in humans, it may be beneficial for the antigen binding domain of the CAR to comprise a human antibody or fragment thereof. Thus, in some embodiments, the antigen binding domain comprises a human antibody or a fragment thereof.

An antigen binding domain (e.g., an scFV) that "specifically binds" to a target or an epitope is a term understood in the art, and methods to determine such specific binding are also known in the art. A molecule is said to exhibit "specific binding" if it reacts or associates more frequently, more rapidly, with greater duration and/or with greater affinity with a particular target antigen than it does with alternative targets. An antibody "specifically binds" to a target antigen if it binds with greater affinity, avidity, more readily, and/or with greater duration than it binds to other substances. For example, an antigen binding domain (e.g., an scFV) that specifically binds to TSHR or an epitope therein is an antibody that binds this target antigen with greater affinity, avidity, more readily, and/or with greater duration than it binds to other antigens or other epitopes in the same antigen. It is also understood by reading this definition that, for example, an antigen binding domain (e.g., an scFV) that specifically binds to a first target antigen may or may not specifically bind to a second target antigen. As such, "specific binding" does not necessarily require (although it can include) exclusive binding. Generally, but not necessarily, reference to binding means specific binding. In some embodiments, antigen binding domains (e.g., scFVs) described herein have a suitable binding affinity to TSHR. As used herein, "binding affinity" refers to the apparent association constant or $K_A$. The $K_A$ is the reciprocal of the dissociation constant ($K_D$). The antibody described herein may have a binding affinity ($K_A$) of at least $10^5$, $10^6$, $10^7$, $10^8$, $10^9$, $10^{10}$ M, or higher. An increased binding affinity corresponds to a decreased $K_D$. Higher affinity binding of an antibody to a first target relative to a second target can be indicated by a higher $K_A$ (or a smaller numerical value $K_D$) for binding the first target than the $K_A$ (or numerical value $K_D$) for binding the second target. In such cases, the antibody has specificity for the first target relative to the second target. Differences in binding affinity (e.g., for specificity or other comparisons) can be at least 1.5, 2, 3, 4, 5, 10, 15, 20, 37.5, 50, 70, 80, 91, 100, 500, 1000, 10,000 or $10^5$ fold.

Binding affinity can be determined by a variety of methods including equilibrium dialysis, equilibrium binding, gel filtration, ELISA, surface plasmon resonance, or spectroscopy (e.g., using a fluorescence assay). Examples of conditions for evaluating binding affinity are in, e.g., TRIS-buffer (50 mM TRIS, 150 mM NaCl, 5 mM CaCl2 at pH7.5). These techniques can be used to measure the concentration of bound binding protein as a function of target protein concentration. The concentration of bound binding protein ([Bound]) is related to the concentration of free target protein ([Free]) and the concentration of binding sites for the binding protein on the target where (N) is the number of binding sites per target molecule by the following equation:

[Bound]=[$N$][Free]/($Kd$+[Free])

It is not always necessary to make an exact determination of $K_A$, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

For in vivo use of antibodies in humans, it may be preferable to use human antibodies. Completely human antibodies are particularly desirable for therapeutic treatment of human subjects. Human antibodies can be made by a variety of methods known in the art including phage display methods using antibody libraries derived from human immunoglobulin sequences, including improvements to these techniques. See, also, U.S. Pat. Nos. 4,444,887 and 4,716,111; and PCT publications WO 98/46645, WO 98/50433, WO 98/24893, WO98/16654, WO 96/34096, WO 96/33735, and WO91/10741; each of which is incorporated herein by reference in its entirety. A human antibody can also be an antibody wherein the heavy and light chains are encoded by a nucleotide sequence derived from one or more sources of human DNA. Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the disclosure.

Antibodies directed against an antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For a detailed discussion of this technology for producing human antibodies and human monoclonal antibodies and protocols for producing such antibodies, see, e.g., PCT Publication Nos. WO2014/055771, WO 98/24893, WO 96/34096, and WO 96/33735; and U.S. Pat. Nos. 5,413,923; 5,625,126; 5,633,425; 5,569,825; 5,661,016; 5,545,806; 5,814,318; and 5,939,598, each of which is incorporated by reference herein in their entirety.

A "humanized" antibody retains a similar antigenic specificity as the original antibody, i.e., in the present disclosure, the ability to bind an antigen described herein, for example, TSHR.

Example of TSHR scFv

In one embodiment, the TSHR directed scFv comprises the following six CDRs:

```
                              (SEQ ID NO: 11)
NYWMN (SEQ ID NO: 12)
RIDPSDSETHYNQNFKD

SGY (SEQ ID NO: 14)
KSSQSLLDSDGKTYLN (SEQ ID NO: 15)
LVSKVDS (SEQ ID NO: 16)
WQGTHSPLT
```

Further Extracellular Domain

In some embodiments, the CAR is designed to include an extracellular T cell co-stimulatory domain such as CD28 extracellular domain, or a portion thereof. The extracellular domain may serve as a hinge domain or T cell activation domain. Examples include the CD28 extracellular domain, which has 50 amino acids. An example of a sequence of the CD28 extracellular domain is:

```
                              (SEQ ID NO: 17)
YVNQTDIYFCKIEVMYPPPYLDNEKSNGTIIHVKGKHLCPSPLFPGPSKP.
```

Transmembrane Domain

With respect to the transmembrane domain, the CAR can be designed to comprise a transmembrane domain that is fused to the extracellular domain (e.g., the antigen binding domain) of the CAR. Any transmembrane domain is contemplated for use herein as long as the domain is capable of anchoring a CAR comprising the domain to a cell membrane. In some embodiments, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex. One skilled in the art would appreciate that the full transmembrane domain, or portion thereof, is implemented with the cytoplasmic domain, or a portion thereof. Typically, the transmembrane and cytoplasmic domains used would be contiguous portions of the CD28 sequence.

The transmembrane domain may be derived either from a natural or from a synthetic source. Where the source is natural, the domain may be derived from any membrane-bound or transmembrane protein. Transmembrane domains of particular use in this disclosure may be derived from (e.g., comprise at least the transmembrane domain(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, and CD154. Transmembrane domains can be identified using any method known in the art or described herein, e.g., by using the UniProt Database.

In some embodiments, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

In some embodiments, the transmembrane domain in a CAR as described by the disclosure is the CD8 transmembrane domain. Sequences of CD8 for this purposes are taught in PCT pub no. WO2014/055771.

In some embodiments, the transmembrane domain in a CAR as described by the disclosure is a CD28 transmembrane domain. An example of a sequence of CD28 is provided below, as well as an example of a transmembrane domain sequence. In some embodiments, the CD28 transmembrane domain comprises the example of a transmembrane domain sequence below, or a fragment or variant thereof that is capable of anchoring a CAR comprising the sequence to a cell membrane.

CD28 (amino acids 19-220)
(SEQ ID NO: 18)
NKILVKQSPMLVAYDNAVNLSCKYSYNLFSREFRASLHKGLDSAVEV

CVVYGNYSQQLQVYSKTGFNCDGKLGNESVTFYLQNLYVNQTDIYFC

KIEVMYPPPYLDNEKSNGTIIHVKGKHLCPSPLFPGPSKPFWVLVVV

GGVLACYSLLVTVAFIIFWVRSKRSRLLHSDYMNMTPRRPGPTRKHY

QPYAPPRDFAAYRS

CD28 (amino acids 153-179, transmembrane domain)
(SEQ ID NO: 19)
FWVLVVVGGVLACYSLLVTVAFIIFWV In some embodiments, a CAR as described by the disclosure comprises a region of CD28 that contains all or part of an extracellular domain, all or part of a transmembrane domain and all or part of a cytoplasmic domain. An example of a region of CD28 for inclusion in a CAR is provided below. In some embodiments, the CD28 transmembrane domain comprises the example of a transmembrane domain sequence below, or a fragment or variant thereof that is capable of anchoring a CAR comprising the sequence to a cell membrane.

CD28 region
(SEQ ID NO: 20)
IEVMYPPPYLDNEKSNGTIIHVKGKHLCPSPLFPGPSKPFWVLVVVGG

VLACYSLLVTVAFIIFWVRSKRSRLLHSDYMNMTPRRPGPTRKHYQPY

APPRDFAAYRSAS

In some embodiments, the transmembrane domain of a CAR as described by the disclosure comprises a hinge domain such as a CD8 hinge domain. An example of a CD8 hinge domain sequence is provided below. In some embodiments, the CD8 hinge domain comprises the example of a sequence shown below, or a fragment or variant thereof that is capable of providing flexibility to or preventing steric hindrance of the CAR or the domain(s) attached to the hinge domain. In some instances, a variety of human hinges can be employed as well including the human Ig (immunoglobulin) hinge.

CD8 hinge domain
(SEQ ID NO: 21)
AKPTTTPAPRPPTPAPTIASQPLSLRPEACRPAAGGAVHTRGLDFACD Cytoplasmic Domain In some embodiments, the cytoplasmic domain or otherwise the intracellular signaling domain of a CAR as described by the disclosure is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire domain. To the extent that a truncated portion of the intracellular signaling domain is used, such truncated portion may be used in place of the intact domain as long as it transduces the effector function signal. The term intracellular signaling domain is thus meant to include any truncated portion of the intracellular signaling domain sufficient to transduce the effector function signal.

In some embodiments, the cytoplasmic domain comprises an IL-15Rα cytoplasmic domain. In some embodiments, the intracellular IL-15Rα cytoplasmic domain displays effector signaling function that enhances immune effector activities including, but not limited to cell proliferation and cytokine production. An example of a IL-15Rα cytoplasmic domain sequence is provided below. In some embodiments, the IL-15Rα cytoplasmic domain comprises the example of a sequence shown below, or a fragment or variant thereof that, when included in a CAR, has the same or an improved function (such as cytolytic activity, cell proliferation or secretion of cytokines) compared to a CAR comprising the example of a sequence shown below. The function may be tested using any suitable method known in the art.

IL-15Rα intracellular domain
(SEQ ID NO: 22)
KSRQTPPLASVEMEAMEALPVTWGTSSRDEDLENCSHHL In some embodiments, the cytoplasmic domain comprises a CD137 intracellular domain (e.g., CD137 cytoplasmic domain). In some embodiments, the intracellular CD137 cytoplasmic domain displays T-cell survival function that enhances the persistence of the immune effector cells. An example of a CD137 cytoplasmic domain sequence is provided below. In some embodiments, the CD137 cytoplasmic domain comprises the example of a sequence shown below, or a fragment or variant thereof that, when included in a CAR, has the same or an improved function (such as T cell proliferation, IL-2 secretion, survival and cytolytic activity)

compared to a CAR comprising the sequence example shown below. The function may be tested using any suitable method known in the art.

In some embodiments, the cytoplasmic domain comprises a CD27 intracellular domain (e.g., CD27 cytoplasmic domain). In some embodiments, the intracellular CD27 cytoplasmic domain displays effector signaling function that enhances immune effector activities including, but not limited to cell proliferation and cytokine production. An example of a CD27 cytoplasmic domain sequence is provided below. In some embodiments, the CD27 cytoplasmic domain comprises the example of a sequence shown below, or a fragment or variant thereof that, when included in a CAR, has the same or an improved function (such as cytolytic activity, cell proliferation or secretion of cytokines) compared to a CAR comprising the sequence example below. The function may be tested using any suitable method known in the art.

CD27 intracellular domain
(SEQ ID NO: 23)
QRRKYRSNKGESPVEPAEPCHYSCPREEEGSTIPIQEDYRKPEPACSP Examples of other intracellular signaling domains for use in the CAR as described by the disclosure include the cytoplasmic sequences of the T cell receptor (TCR) and co-receptors that act in concert to initiate signal transduction following antigen receptor engagement, as well as any fragment or variant of these sequences and any synthetic sequence that has the same functional capability.

It is known that signals generated through the endogenous TCR alone are insufficient for full activation of the T cell and that a secondary or co-stimulatory signal is also required. Thus, T cell activation can be mediated by two distinct classes of cytoplasmic signaling sequences: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences that are of particular use in the disclosure include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the CAR as described by the disclosure comprises a cytoplasmic signaling sequence derived from CD3zeta. Examples of CD3 zeta domain sequences are provided below. In some embodiments, the CD3zeta signaling domain comprises one of the sequence examples below, or a fragment or variant thereof that, when included in a CAR, has the same or an improved function (such as cytolytic activity or secretion of cytokines) compared to a CAR comprising the sequence example below. The function may be tested using any suitable method known in the art.

CD3 zeta signaling domain
(SEQ ID NO: 24)
RVKFSRSADAPAYKQGQNQLYNELNLGRREEYDVLDKRRGRDPEMGGK

PRRKNPQEGLYNELQKDKMAEAYSEIGMKGERRRGKGHDGLYQGLSTA

TKDTYDALHMQALPPR

CD3 zeta signaling domain
(SEQ ID NO: 25)
RVKFSRSADAPAYQQGQNQLYNELNLGRREEYDVLDKRRGRDPEMGGK

PRRKNPQEGLYNELQKDKMAEAYSEIGMKGERRRGKGHDGLYQGLSTA

TKDTYDALHMQALPPR

The cytoplasmic domain of the CAR can be designed to comprise a CD3-zeta signaling domain combined with any other desired cytoplasmic domain(s) useful in the context of a CAR as described by the disclosure. For example, the cytoplasmic domain of the CAR can comprise a CD3 zeta domain and a costimulatory signaling region. The costimulatory signaling region refers to a portion of the CAR comprising the intracellular domain of a costimulatory molecule. Thus, while CARs described by the disclosure are exemplified primarily with CD28, CD137, CD27 and CD3z as the co-stimulatory and signaling elements, other additional costimulatory elements are within the scope of the disclosure. Non-limiting examples of co-stimulatory signaling regions include 4-1BB (also referred to as CD137), CD21, CD127, ICOS, IL-15Rα, and OX40.

In some embodiments, the cytoplasmic domain of a CAR can be designed to comprise an IL-15Rα cytoplasmic domain and a CD3-zeta signaling domain combined with any other desired cytoplasmic domain(s) useful in the context of a CAR as described by the disclosure. For example, the cytoplasmic domain of the CAR can comprise an IL-15Rα cytoplasmic domain, a CD3 zeta domain and a costimulatory signaling region. The costimulatory signaling region refers to a portion of the CAR comprising the intracellular domain of a costimulatory molecule. Thus, while CARs as described by the disclosure are exemplified primarily with CD28-CD137-CD27-CD3z as the co-stimulatory and signaling element, other additional costimulatory elements are within the scope of the disclosure.

The cytoplasmic domain of the CAR can be designed to comprise CD27 cytoplasmic domain and a CD3-zeta signaling domain combined with any other desired cytoplasmic domain(s) useful in the context of the CAR of the disclosure. For example, the cytoplasmic domain of the CAR can comprise CD27 cytoplasmic domain, a CD3 zeta domain and a costimulatory signaling region. The costimulatory signaling region refers to a portion of the CAR comprising the intracellular domain of a costimulatory molecule. Example sequences of co-stimulatory signaling regions are shown below.

CD28 (amino acids 180-220, cytoplasmic domain)
(SEQ ID NO: 26)
RSKRSRLLHSDYMNMTPRRPGPTRKHYQPYAPPRDFAAYRS 4-1BB (CD137) intracellular TRAF binding domain
(SEQ ID NO: 27)
KRGRKKLLYIFKQPFMRPVQTTQEEDGCSCRFPEEEEGGCEL ICOS intracellular domain
(SEQ ID NO: 28)
CWLTKKKYSSSVHDPNGEYMFMRAVNTAKKSRLTDVTL OX40 intracellular domain
(SEQ ID NO: 29)
ALYLLRRDQRLPPDAHKPPGGGSFRTPIQEEQADAHSTLAKI CD27 intracellular domain
(SEQ ID NO: 23)
QRRKYRSNKGESPVEPAEPCHYSCPREEEGSTIPIQEDYRKPEPACSP CD127 intracellular domain
(SEQ ID NO: 31)
KRIKPIVWPSLPDHKKTLEHLCKKPRKNLNVSFNPESFLDCQIHRVDD

IQARDEVEGFLQDTFPQQLEESEKQRLGGDVQSPNCPSEDVVITPESF

GRDSSLTCLAGNVSACDAPILSSSRSLDCRESGKNGPHVYQDLLLSLG

TTNSTLPPPFSLQSGILTLNPVAQGQPILTSLGSNQEEAYVTMSSFYQ

NQ

IL-15Rα intracellular domain
(SEQ ID NO: 22)
KSRQTPPLASVEMEAMEALPVTWGTSSRDEDLENCSHHL In some embodiments, a CAR as described by the disclosure comprises the apoptosis inducing gene Casp9 or a domain or truncated version thereof, for example as described by Straathoff et al. *Blood*, June 1; 105(11): 4247-4254 (2005). An example of a Casp9 sequence and truncated sequence is below. In some embodiments, the CAR comprises a 2A peptide linker between a CD3 zeta domain and Casp9.

CASP9 amino acid sequence
(SEQ ID NO: 32)
MDEADRRLLRRCRLRLVEELQVDQLWDALLSRELFRPHMIEDIQRAGS

GSRRDQARQLIIDLETRGSQALPLFISCLEDTGQDMLASFLRTNRQAA

KLSKPTLENLTPVVLRPEIRKPEVLRPETPRPVDIGSGGFGDVGALES

LRGNADLAYILSMEPCGHCLIINNVNFCRESGLRTRTGSNIDCEKLRR

RFSSLHFMVEVKGDLTAKKMVLALLELAQQDHGALDCCVVVILSHGCQ

ASHLQFPGAVYGTDGCPVSVEKIVNIFNGTSCPSLGGKPKLFFIQACG

GEQKDHGFEVASTSPEDESPGSNPEPDATPFQEGLRTFDQLDAISSLP

TPSDIFVSYSTFPGFVSWRDPKSGSWYVETLDDIFEQWAHSEDLQSLL

LRVANAVSVKGIYKQMPGCFNFLRKKLFFKTS

A truncated CASP9 amino acid sequence
(SEQ ID NO: 33)
VGALESLRGNADLAYILSMEPCGHCLIINNVNFCRESGLRTRTGSNID

CEKLRRRFSSLHFMVEVKGDLTAKKMVLALLELAQQDHGALDCCVVVI

LSHGCQASHLQFPGAVYGTDGCPVSVEKIVNIFNGTSCPSLGGKPKLF

FIQACGGEQKDHGFEVASTSPEDESPGSNPEPDATPFQEGLRTFDQLD

AISSLPTPSDIFVSYSTFPGFVSWRDPKSGSWYVETLDDIFEQWAHSE

DLQSLLLRVANAVSVKGIYKQMPGCFNFLRKKLFFKTS

In some embodiments, a CAR further comprises a mutated FK506 binding protein (e.g., FKBPf36v) motif. An example of a mutated FK506 binding protein motif is provided below.

FKBP f36v amino acid sequence
(SEQ ID NO: 34)
MGVQVETISPGDGRTFPKRGQTCVVHYTGMLEDGKKVDSSRDRNKPFK

FMLGKQEVIRGWEEGVAQMSVGQRAKLTISPDYAYGATGHPGIIPPHA

TLVFDVELLKLE

The cytoplasmic signaling sequences within the cytoplasmic signaling portion of a CAR as described by the disclosure may be linked to each other in a random or specified order. Optionally, a short oligo- or polypeptide linker or spacer, preferably between 5 and 20 amino acids in length may be inserted between cytoplasmic domains. A GGGGS (SEQ ID NO: 37) or (GGGGS)×3 (SEQ ID NO: 2) provides a particularly suitable linker.

In some embodiments, a CAR comprises or consists of the sequence below, which is broken down by examples of domains included therein (domain names appear in bold after each domain in the examples of CARs):

(CD28 transmembrane domain)
(SEQ ID NO: 35)
FWVLVVVGGVLACYSLLVTVAFIIFWV (4-1BB intracellular domain)
(SEQ ID NO: 27)
KRGRKKLLYIFKQPFMRPVQTTQEEDGCSCRFPEEEEGGCEL (CD27 intracellular domain)
(SEQ ID NO: 23)
QRRKYRSNKGESPVEPAEPCHYSCPREEEGSTIPIQEDYRKPEPACSP (Linker)
(SEQ ID NO: 4)
GSTSGSGKPGSSEGSTKG (CD3 zeta domain)
(SEQ ID NO: 24)
RVKFSRSADAPAYKQGQNQLYNELNLGRREEYDVLDKRRGRDPEMGGK

PRRKNPQEGLYNELQKDKMAEAYSEIGMKGERRRGKGHDGLYQGLSTA

TKDTYDALHMQALPPR (Linker)
(SEQ ID NO: 4)
GSTSGSGKPGSSEGSTKG (truncated iCasp9 domain)
(SEQ ID NO: 36)
VGALESLRGNADLAYILSMEPCGHCLIINNVNFCRESGLRTRTGSNID

CEKLRRRFSSLHFMVEVKGDLTAKKMVLALLELAQQDHGALDCCVVVI

LSHGCQASHLQFPGAVYGTDGCPVSVEKIVNIFNGTSCPSLGGKPKLF

FIQACGGEQKDHGFEVASTSPEDESPGSNPEPDATPFQEGLRTFDQLD

AISSLPTPSDIFVSYSTFPGFVSWRDPKSGSWYVETLDDIFEQWAHSE

DLQSLLLRVANAVSVKGIYKQMPGCFNFLRKKLFFKTS (FKBP domain)
(SEQ ID NO: 34)
MGVQVETISPGDGRTFPKRGQTCVVHYTGMLEDGKKVDSSRDRNKPFK

FMLGKQEVIRGWEEGVAQMSVGQRAKLTISPDYAYGATGHPGIIPPHA

TLVFDVELLKLE

In some embodiments, the above non-limiting examples of arrangements are from left to right, N-terminus to C-terminus of the CAR. The CAR may comprise or further comprise any other combination of elements as described herein.

Vectors

In some embodiments, the disclosure encompasses a DNA construct comprising sequences of a CAR, wherein the sequence comprises the nucleic acid sequence of an antigen binding domain operably linked to the nucleic acid sequence of transmembrane domain and a cytoplasmic domain. An example of a cytoplasmic domain that can be used in a CAR as described by the disclosure includes but is not limited to the cytoplasmic domain of CD28 and the signaling domain of CD3-zeta. In some embodiments, a CAR comprises the intracellular domain of CD28, 4-1BB (CD137), and/or CD27 and the signaling domain of CD3-zeta. In some instances, a CAR can further comprise the apoptosis inducing gene Casp9.

In some embodiments, the arrangement of the elements of the CAR is selected from one of the following non-limiting examples of arrangements:
TSHRscFv-CD28-IL-15Rα-CD3z
TSHRscFv-CD28-CD27-IL-15Rα-CD3z
TSHRscFv-CD28-(4-1BB)-CD27-IL-15Rα-CD3z
TSHRscFv-CD8-CD27-IL-15Rα-CD3z
TSHRscFv-CD8-(4-1BB)-CD27-IL-15Rα-CD3z
TSHRscFv-CD28-(4-1BB)-CD27-CD3z-iCasp9-FKBP
TSHRscFv-CD28-CD27-(4-1BB)-CD3z-iCasp9-FKBP
TSHRscFv-CD8-(4-1BB)-CD27-CD3z-iCasp9-FKBP
TSHRscFv-CD8-CD27-(4-1BB)-CD3z-iCasp9-FKBP
TSHRscFv-CD28-(4-1BB)-CD27-CD3z
TSHRscFv-CD8-CD28-CD3z
TSHRscFv-CD28-(4-1BB)-CD27-CD3z-Casp9-FKBP
TSHRscFv-CD8-CD28-CD3z-Casp9-FKBP
TSHRscFv-CD28-CD137-CD27-CD3z-2A-iCasp9

In some embodiments, the above non-limiting examples of arrangements are from left to right, N-terminus to C-terminus of the CAR. The CAR may comprise or further comprise any other combination of elements as described herein.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present disclosure also provides vectors in which a DNA of the present disclosure is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In another embodiment, the desired CAR can be expressed in the cells by way of transposons.

Expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration into eukaryotes. Typical cloning vectors contain transcription and translation terminators, initiation sequences, and promoters useful for regulation of the expression of the desired nucleic acid sequence. The expression constructs of the disclosure may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the disclosure provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, retrovirus vectors are used. A number of retrovirus vectors are known in the art. In some embodiments, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Factor-1a (EF-1a). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the disclosure is not limited to the use of constitutive promoters. Inducible promoters are also contemplated as part of the disclosure. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. In some embodiments, the promoter is a EF-1a promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like, and fluorescent genes such as GFP, YFP, RFP and the like. In some embodiments, reporter genes or selectable marker genes are excluded from a CAR polypeptide used in a therapy as described herein.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity, antibiotic resistance or fluorescence. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means. In some embodiments, the host cell is a T cell.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An example of a colloidal system for use as a delivery vehicle in vitro and in vivo is a liposome (e.g., an artificial membrane vesicle).

In the case where a non-viral delivery system is utilized, an example of a delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the disclosure, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the disclosure.

RNA Transfection

In some embodiments, the genetically modified T cells of the disclosure are modified through the introduction of RNA (e.g., an mRNA comprises a sequence encoding a CAR as described herein). In some embodiments, an in vitro transcribed RNA CAR can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is a CAR as described by the disclosure.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Genetically Modified Immune Cells

In some embodiments, the CAR sequence(s) (e.g., nucleic acid sequences encoding a CAR as described herein) are delivered into cells (e.g., T cells or NK cells) using a retroviral or lentiviral vector. In some embodiments, the arrangement of the elements of the CAR encoded by the CAR sequence(s) is selected from one of the following non-limiting examples of arrangements:

TSHRscFv-CD28-IL-15Rα-CD3z
TSHRscFv-CD28-CD27-IL-15Rα-CD3z
TSHRscFv-CD28-(4-1BB)-CD27-IL-15Rα-CD3z
TSHRscFv-CD8-CD27-IL-15Rα-CD3z
TSHRscFv-CD8-(4-1BB)-CD27-IL-15Rα-CD3z
TSHRscFv-CD28-(4-1BB)-CD27-CD3z-iCasp9-FKBP
TSHRscFv-CD28-CD27-(4-1BB)-CD3z-iCasp9-FKBP
TSHRscFv-CD8-(4-1BB)-CD27-CD3z-iCasp9-FKBP
TSHRscFv-CD8-CD27-(4-1BB)-CD3z-iCasp9-FKBP
TSHRscFv-CD28-(4-1BB)-CD27-CD3z
TSHRscFv-CD8-CD28-CD3z
TSHRscFv-CD28-(4-1BB)-CD27-CD3z-Casp9-FKBP
TSHRscFv-CD8-CD28-CD3z-Casp9-FKBP
TSHRscFv-CD28-CD137-CD27-CD3z-2A-iCasp9

In some embodiments, the above non-limiting examples of arrangements are from left to right, N-terminus to C-terminus of the CAR. The CAR may comprise or further comprise any other combination of elements as described herein.

CAR-expressing retroviral and lentiviral vectors can be delivered into different types of eukaryotic cells as well as into tissues and whole organisms using transduced cells as carriers or cell-free local or systemic delivery of encapsulated, bound or naked vectors. The method used can be for any purpose where stable expression is required or sufficient.

In another embodiment, the desired CAR can be expressed in the cells (e.g., T cells or NK cells) by way of transposons.

The disclosed methods can be applied to the modulation of immune cell (e.g., T cell or NK cell) activity in basic research and therapy, in the fields of cancer, stem cells, acute and chronic infections, and autoimmune diseases, including the assessment of the ability of the genetically modified T cell or NK cell to kill a target cell, e.g., a target cancer cell.

In some embodiments, methods described by the disclosure also provide the ability to control the level of expression over a wide range by changing, for example, the promoter or the amount of input vector, making it possible to individually regulate the expression level. For example, varying of different intracellular effector/costimulator domains on multiple chimeric receptors in the same cell allows determination of the structure of the receptor combinations which assess the highest level of cytotoxicity against multi-antigenic targets, and at the same time lowest cytotoxicity toward normal cells.

Sources of Immune Cells

Prior to expansion and genetic modification of the immune cells (e.g., T cells) of the disclosure, a source of immune cells (e.g., T cells) is obtained from a subject. Immune cells (e.g., T cells) can be obtained from a number of sources, including peripheral blood mononuclear cells, bone marrow, lymph node tissue, cord blood, thymus tissue, tissue from a site of infection, ascites, pleural effusion, spleen tissue, and tumors. The immune cells (e.g., T cells) may also be generated from induced pluripotent stem cells or hematopoietic stem cells or progenitor cells. In some embodiments, any number of immune cell lines, including but not limited to T cell and NK cell lines, available in the art, may be used. In some embodiments, immune cells (e.g., T cells) can be obtained from a unit of blood collected from a subject using any number of techniques known to the skilled artisan, such as Ficoll™ separation. In some embodiments, cells from the circulating blood of an individual are obtained by apheresis. The apheresis product typically contains lymphocytes, including T cells, monocytes, granulocytes, B cells, NK cells, other nucleated white blood cells, red blood cells, and platelets. In some embodiments, the cells collected by apheresis may be washed to remove the plasma fraction and to place the cells in an appropriate buffer or media for subsequent processing steps. In some embodiments, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed and the cells directly resuspended in culture media.

In some embodiments, immune cells (e.g., T cells) are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as CD3$^+$, CD28$^+$, CD4$^+$, CD8$^+$, CD45RA$_+$, and CD45RO$^+$ T cells, can be further isolated by positive or negative selection techniques. For example, in some embodiments, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In some embodiments, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this disclosure. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4$^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express CD4$^+$, CD25$^+$, CD62L$^{hi}$, GITR$^+$, and FoxP3$^+$.

Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in some embodiments, a concentration of 2 billion cells/ml is used. In some embodiments, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (e.g., leukemic blood, tumor tissue, etc.). Such populations of cells may have therapeutic value and would be desirable to obtain. For example, using high concentration of cells allows more efficient selection of CD8$^+$T cells that normally have weaker CD28 expression.

In some embodiments, it is desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4$^+$ T cells express higher levels of CD28 and are more efficiently captured than CD8$^+$ T cells in dilute concentrations. In some embodiments, the concentration of cells used is 5×10$^6$/ml. In other embodiments, the concentration used can be from about 1×10$^5$/ml to 1×10$^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen. In certain embodiments, cryopreserved cells are thawed and washed as described herein and allowed to rest for one hour at room temperature prior to activation using the methods of the disclosure.

Also contemplated in the context of the disclosure is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In some embodiments a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, Cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In some embodiments, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present disclosure to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

Whether prior to or after genetic modification of the T cells to express a desirable CAR, the T cells can be activated and expanded generally using methods as described, for example, in U.S. Pat. Nos. 6,352,694 and 6,534,055.

Generally, the T cells of the disclosure are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibodies include 9.3, B-T3, XR-CD28 (Diaclone, Besancon, France), which can be used, as can other methods commonly known in the art (Berg et al., Transplant Proc. 30(8):3975-3977, 1998; Haanen et al., J. Exp. Med. 190(9): 13191328, 1999; Garland et al., J. Immunol Meth. 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In some embodiments, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells as described by the disclosure.

In some embodiments, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In some embodiments, a 1:1 ratio of each antibody bound to the beads for $CD4^+$ T cell expansion and T cell growth is used. In certain aspects, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In some embodiments, the ratio of CD3:CD28 antibody bound to the beads ranges from 100:1 to 1:100 and all integer values there between. In some embodiments, more anti-CD28 antibody is bound to the particles than anti-CD3 antibody, i.e., the ratio of CD3:CD28 is less than one. In some embodiments, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3

CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In some embodiments, a ratio of particles to cells of 1:1 or less is used. In one particular embodiment, a preferred particle:cell ratio is 1:5. In further embodiments, the ratio of particles to cells can be varied depending on the day of stimulation. For example, in some embodiments, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in methods described by the disclosure. In particular, ratios will vary depending on particle size and on cell size and type.

In some embodiments, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In some embodiments the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the disclosure. In certain embodiments, it may be desirable to significantly decrease the volume in which particles and cells are mixed together (i.e., increase the concentration of cells), to ensure maximum contact of cells and particles. For example, in some embodiments, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In some embodiments, the mixture may be cultured for several hours (about 3 hours) to about 14 days or any hourly integer value in between. In another embodiment, the mixture may be cultured for 21 days. In some embodiments, the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFp, and TNF-a or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, a-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population (¾, CD4+) that is greater than the cytotoxic or suppressor T cell population ($T_c$, CD8+). Ex vivo expansion of T cells by stimulating CD3 and CD28 receptors produces a population of T cells that prior to about days 8-9 consists predominately of ¾ cells, while after about days 8-9, the population of T cells comprises an increasingly greater population of Tc cells. Accordingly, depending on the purpose of treatment, infusing a subject with a T cell population comprising predominately of $T_H$ cells may be advantageous. Similarly, if an antigen-specific subset of Tc cells has been isolated it may be beneficial to expand this subset to a greater degree.

Further, in addition to CD4 and CD 8 markers, other phenotypic markers vary significantly, but in large part, reproducibly during the course of the cell expansion process. Thus, such reproducibility enables the ability to tailor an activated T cell product for specific purposes.

Therapeutic Application

In some embodiments, the disclosure provides a cell (e.g., T cell) modified to express a CAR comprises an antigen binding domain, a transmembrane domain (such as CD28 transmembrane domain), and a cytoplasmic domain comprising an IL-15Rα cytoplasmic domain, optionally combined with CD3-zeta and/or any other cytoplasmic domains described herein. In some embodiments, a cell is modified to express a CAR comprising an antigen binding domain, a transmembrane domain (such as CD28 transmembrane domain), and a cytoplasmic domain having a CD27 intracellular domain and a 4-1BB (CD137) intracellular domain, optionally combined with CD3-zeta and/or any other cytoplasmic domains (e.g., an iCasp9 domain) described herein. In some embodiments, a cell is modified to express a CAR comprising an antigen binding domain (e.g., a scFV specific for TSHR), a transmembrane domain (such as CD28 transmembrane domain), and a cytoplasmic domain. Therefore, in some instances, the transduced T cell can elicit a CAR-mediated T-cell response.

In some embodiments, the disclosure includes a type of cellular therapy where T cells are genetically modified to express a CAR and the CAR T cell is infused to a recipient in need thereof. The infused cell is able to kill cells expressing the antigen, e.g., tumor cells, in the recipient. Unlike antibody therapies, CAR T cells are able to replicate in vivo resulting in long-term persistence that can lead to sustained tumor control.

In some embodiments, CAR T cells as described by the disclosure undergo robust in vivo T cell expansion and can persist for an extended amount of time.

While the data disclosed herein specifically disclose lentiviral vector comprising (1) anti-TSHR scFv, a CD28 domain, a CD137 domain, a CD27 domain and a CD3-zeta signaling domain, the disclosure should be construed to include any number of variations for each of the components of the construct combined with a TSHR scFv, as described elsewhere herein. That is, the disclosure includes the use of any combination of transmembrane and intracellular co-signaling and immune cell functional enhancers to generate a CAR-mediated T-cell response specific to TSHR and its cellular substrates. For example, the TSHR binding domain in a CAR as described by the disclosure can target a thyroid tumor cell for the purposes of treating thyroid cancer.

The CAR-modified immune cells (e.g., CAR T cells) of the disclosure may be administered either alone, or as a composition (e.g., a pharmaceutical composition) in combination with diluents and/or with other components such as IL-2 or other cytokines or cell populations. Briefly, pharmaceutical compositions of the disclosure may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants {e.g., aluminum hydroxide); and preservatives.

Compositions of the disclosure are preferably formulated for intravenous administration.

Pharmaceutical compositions of the disclosure may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "therapeutic amount" is indicated, the precise amount of the compositions of the disclosure to be administered can be determined by a physician with consideration of individual differences in age, weight, tumor size, extent of infection or metastasis, and condition of the patient (subject). It can generally be stated that a pharmaceutical composition comprising the CAR-modified immune cells (e.g., CAR T cells) described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319: 1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated immune (e.g., T cells) to a subject and then subsequently redraw blood (or have an apheresis performed), activate T cells therefrom according to the disclosure, and reinfuse the patient with these activated and expanded T cells. This process can be carried out multiple times every few weeks. In certain embodiments, T cells can be activated from blood draws of from 10cc to 400cc. In certain embodiments, T cells are activated from blood draws of 20cc, 30cc, 40cc, 50cc, 60cc, 70cc, 80cc, 90cc, or 100cc. Not to be bound by theory, using this multiple blood draw/multiple reinfusion protocol may serve to select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In some embodiments, the T cell compositions of the disclosure are administered to a patient by intradermal or subcutaneous injection. In another embodiment, the T cell compositions of the disclosure are preferably administered by i.v. injection. The compositions of T cells may be injected directly into a tumor, lymph node, or site of infection.

In some embodiments, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells as described by the disclosure may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). In a further embodiment, the cell compositions of the disclosure are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the disclosure are administered following B-cell ablative therapy such as agents that react with CD20, e.g., Rituxan. For example, in some embodiments, subjects may undergo standard treatment with high dose chemotherapy followed by peripheral blood stem cell transplantation. In certain embodiments, following the transplant, subjects receive an infusion of the expanded immune cells of the disclosure. In an additional embodiment, expanded cells are administered before or following surgery.

In certain embodiments, cells activated and expanded using the methods described herein, or other methods known in the art where T cells are expanded to therapeutic levels, or any other compositions described herein, are administered to a patient in conjunction with (e.g., before, simultaneously or following) any number of relevant treatment modalities, including checkpoint inhibitors, such as PD-L1 inhibitors or PD1 inhibitors. In some embodiments, the PD-L1 inhibitors or PD1 inhibitors are PD-L1-specific antibodies or PD1-specific antibodies. Examples of checkpoint inhibitors include, e.g., pembrolizumab (Merck), ipilimumab (Bristol-Myers Squibb), nivolumab (Bristol-Myers Squibb), MPDL3280A (Roche), MEDI4736 (AstraZeneca), MEDI0680 (AstraZeneca), BMS-936559/MDX-1105 (Bristol-Myers Squibb) and MSB0010718C (Merck). Other PD-L1 and PD1 inhibitors are known in the art (see, e.g., Dolan et al. PD-1 pathway inhibitors: changing the landscape of cancer immunotherapy. Cancer Control. 2014 July; 21(3):231-7). In some embodiments, compositions described herein are administered in conjunction with (e.g., before, simultaneously or following) chemotherapy and/or radiotherapy.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766). Strategies for CAR T cell dosing and scheduling have been discussed (Ertl et al, 2011, Cancer Res, 71:3175-81; Junghans, 2010, Journal of Translational Medicine, 8:55).

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1. Chimeric Antigen Receptor Expressing T Cells Mediate Activity Against Papillary and Follicular Thyroid Cancers (PTC and FTC)

Since surgery and Iodine-131 therapies are not completely effective against thyroid cancers, and Iodine-131 poses significant risks to patients, there is a clear need for the development of targeted therapeutics against refractory thyroid cancers, as well as a need for the development of therapeutics with improved safety profiles. Chimeric antigen receptor (CAR) modified T cells can meet this need by utilizing the immune system's surveillance capacity and potent cytotoxic mechanisms against thyroid tumor specific antigen targets with exquisite specificity, and without incurring the risk of dosing with a dangerous radioactive isotope.

Detection of TSHR Expression

Figure 3:
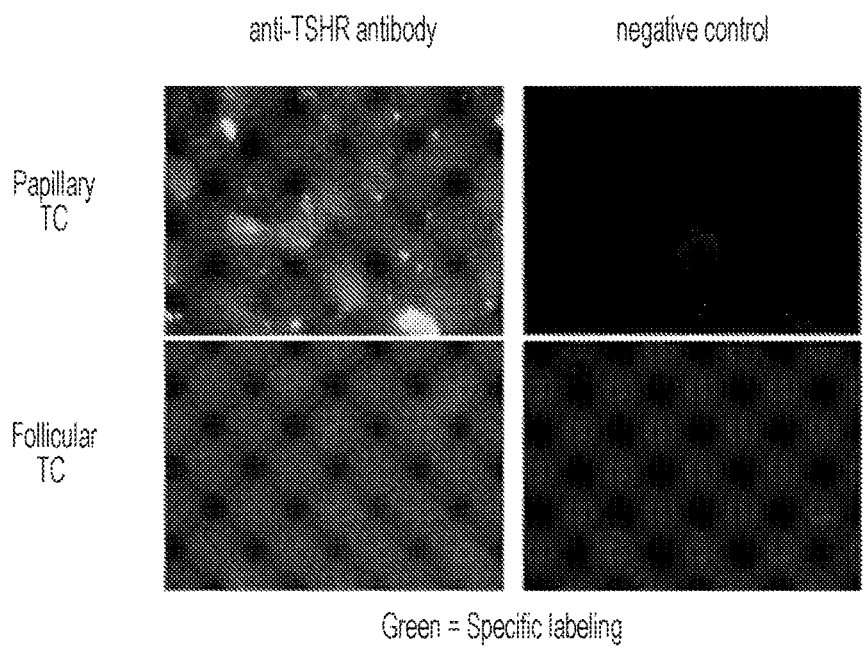
FIG. 3 shows a series of fluorescent micrographs of two types of DTC (papillary TC and follicular TC) labelled with a fluorophore tagged anti-TSHR antibody. No staining is present in negative controls.
Figure 4:
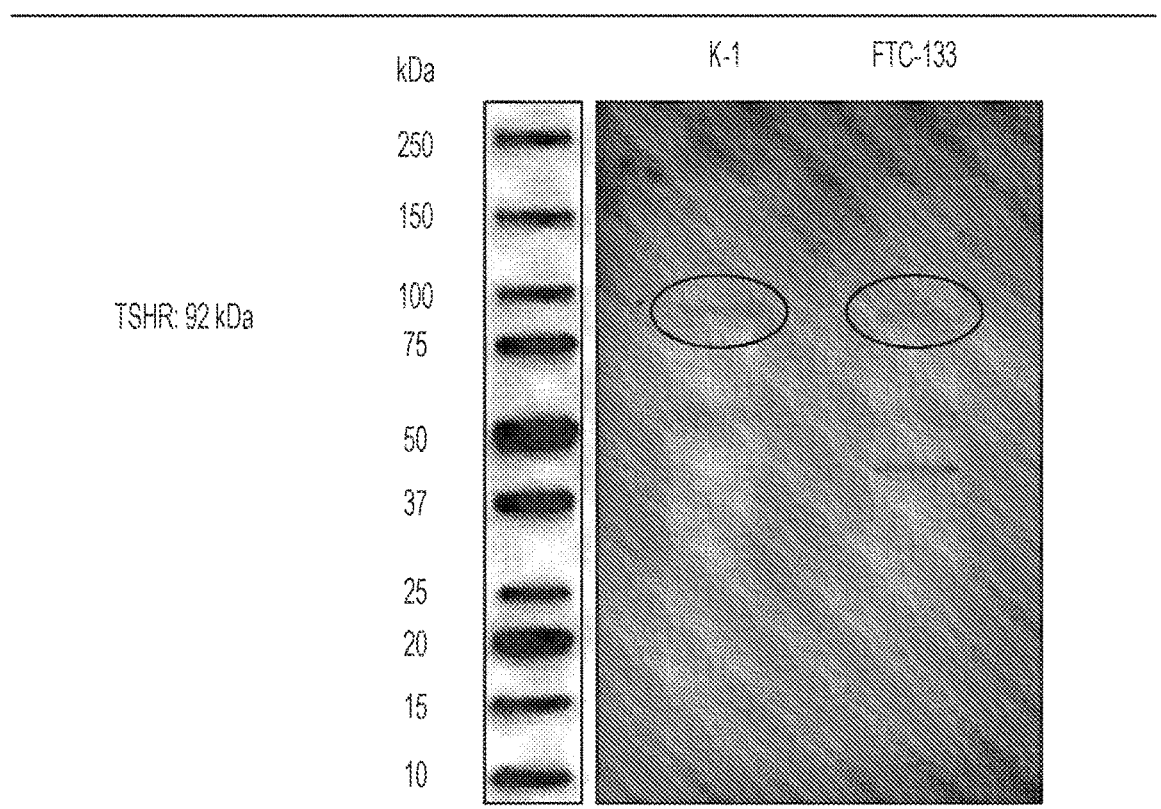
FIG. 4 shows a Western blot of TSHR expression in K-1 and FTC-133 cell lines, as indicated by immune labelling of a 92 kDa molecule with anti-TSHR.
Figure 5:
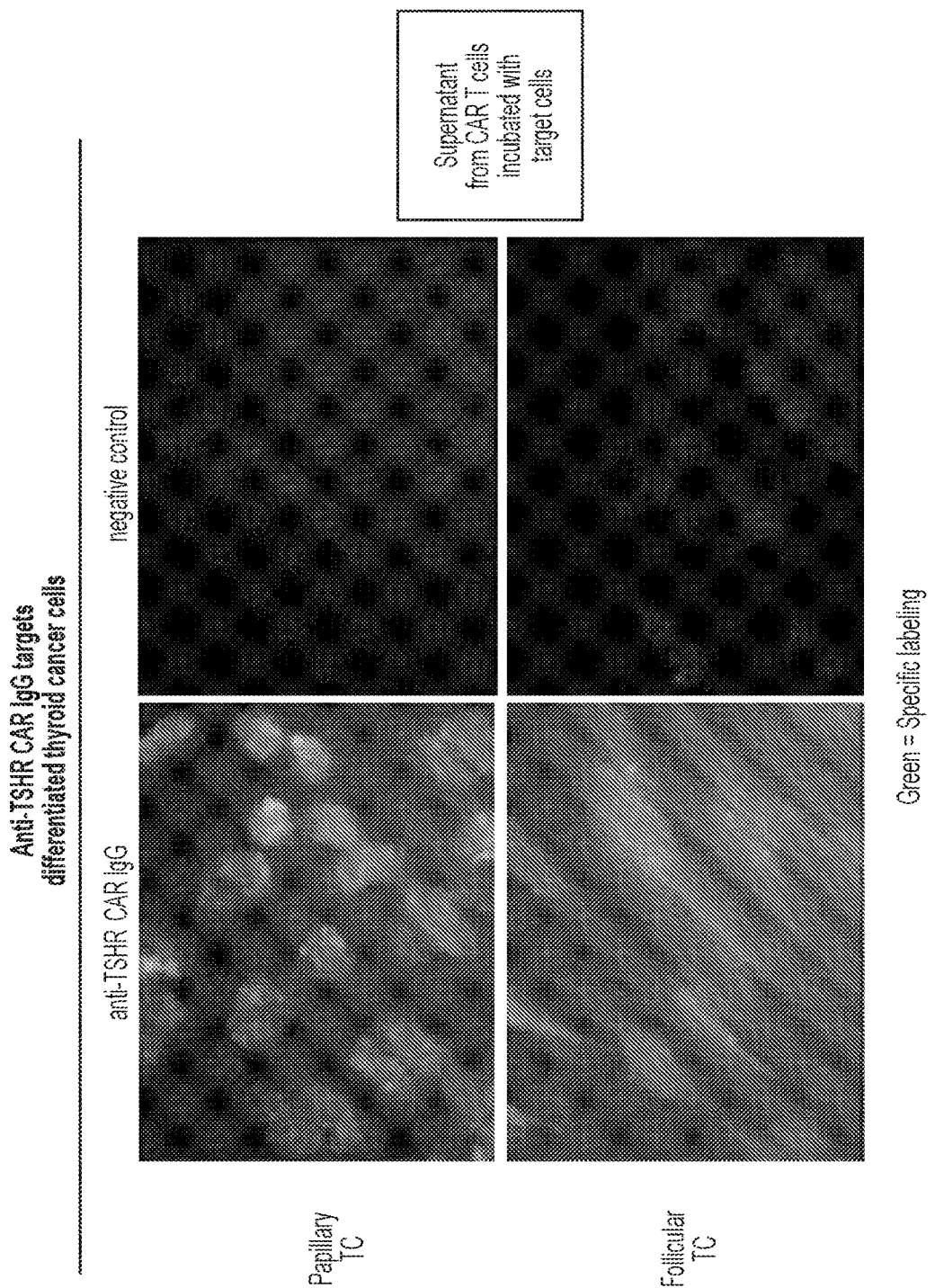
FIG. 5 shows a series of micrographs of papillary and follicular tumor cells labelled with anti-TSHR CAR IgG. No labeling was present in negative controls.

Expression of TSHR on the cell surface of K-1 and FTC-133 thyroid cancer cell lines was assessed using a commercially available anti-TSHR antibody (Abcam, A7 clone) for the which demonstrated TSHR expression in both cell lines (FIG. 3) and no detectable binding to negative controls. Expression of TSHR in the two tumor lines was confirmed by Western Blot (FIG. 4) indicating a 92 kDa species consistent with TSHR, stained positively by anti-TSHR in both cell liners. Finally, fluorescent microscopy demonstrated an anti-TSHR CAR-T labelled both K1 and FTC-133 but did not label negative controls (FIG. 5)

Construction of Lentiviral Vectors

Lentiviral vectors were generated using the NHP/TYF lentiviral vector system. CAR DNA was chemically synthesized and cloned into pTYF transducing vector behind human EF1α promoter using standard molecular cloning approaches. The final lentiviral-constructs were verified by restriction enzyme mapping and DNA sequencing.

Blood Donors, PBMC Isolation and T Cell Activation

Peripheral blood mononuclear cells (PBMCs) were isolated from healthy donors with approval of the Institutional Review Board. T cells were activated using anti-CD3 and anti-CD28 antibodies. These cells were maintained in medium supplemented with IL-2, -7, -15. Surface marker analysis of activated cells was performed to confirm T cell purity and phenotype. After expansion for 2-6 days, T cells were transduced with lentiviral anti-TSHR CAR vectors followed by expansion.

Construction of 4th Generation Anti-TSHR CAR Lentiviral Vectors.

To engineer TSHR-specific CARs, humanized TSHR-specific scFv clones were derived from anti-TSHR monoclonal antibody 3BD10. These CAR sequences were then human codon-optimized and chemically synthesized. To establish 4th generation CARs, several intracellular T cell signaling motifs were incorporated in the CARs, including CD28 transmembrane and cytoplasmic domain, the co-stimulatory 4-1BB intracellular TRAF binding domain (CD137 domain), the CD27 cytoplasmic domain, and the CD3z chain intracellular domain, a 2A peptide sequence, and an inducible apoptosis trigger iCasp9, as illustrated in FIG. 1. These CAR genes were cloned into the lentiviral vector pTYF and packaged into lentiviral particles for gene transfer.

TSHR-CAR-T Cell Cytotoxicity Analyses

Figure 2:
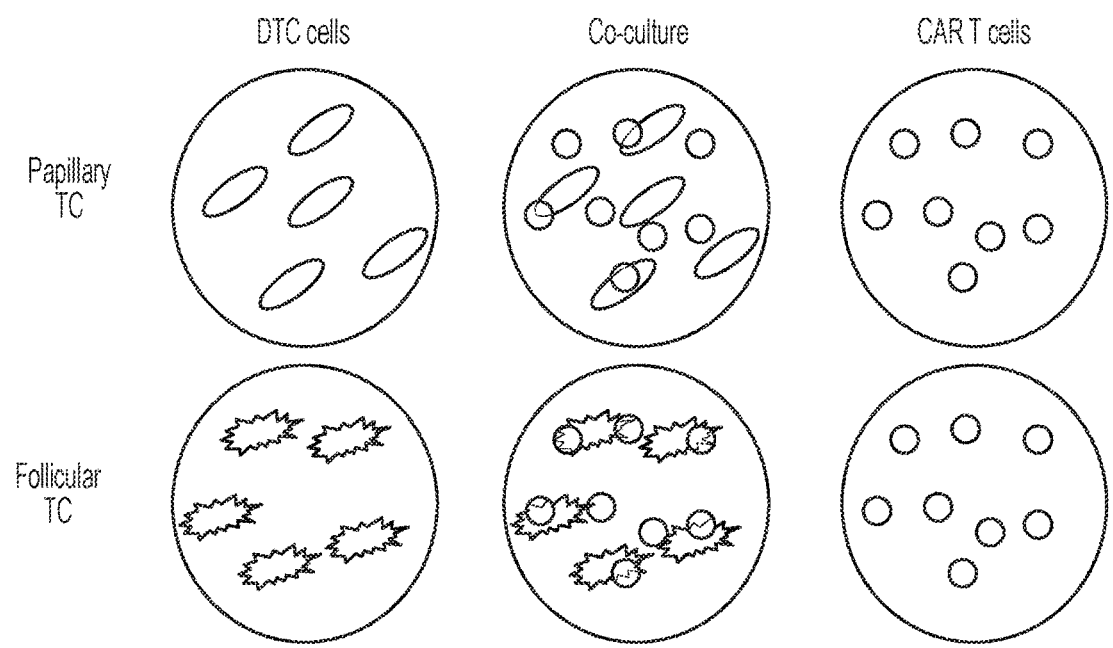
FIG. 2 shows the in-vitro co-culture of two types of differentiated thyroid tumor cells with CAR-T cells leading to the elimination of the tumor cells.
Figure 6:
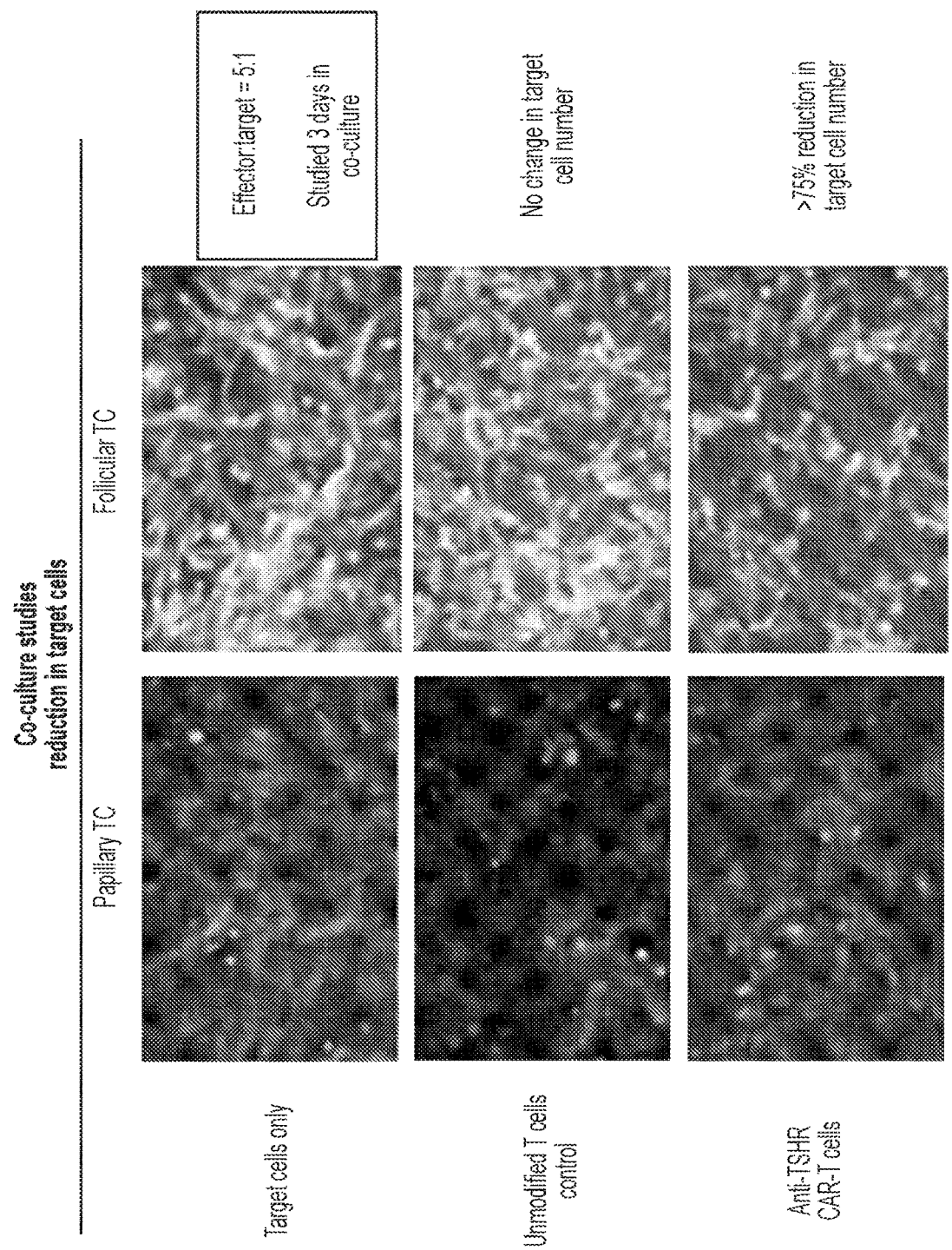
FIG. 6 shows a series of fluorescent micrographs indicating that both papillary and follicular tumor cell populations are significantly depleted by co-culture with anti-TSHR-CAR-T cells but are not depleted by co-culture with unmodified T-cells.

The effectiveness of the anti-TSHR CARTs was determined by co-culturing with K1 or FTC-133 human thyroid cancer cell lines. A schematic of the experimental design is provided in FIG. 2. K-1 is a thyroid papillary carcinoma cell line and FTC-133 is a human follicular thyroid carcinoma. The ability of the anti-TSHR CARTs to induce cell killing was examined in co-cultures with the two human thyroid cancer cell lines. Cell killing was first assessed visually by determining if there were fewer K-1 or FTC-133 cells over time when cultured with anti-TSHR CARTs. After 2 days of co-culture, multiple areas of cell death were observed with the anti-TSHR CARTs and not with controls (FIG. 6).

Figure 7:
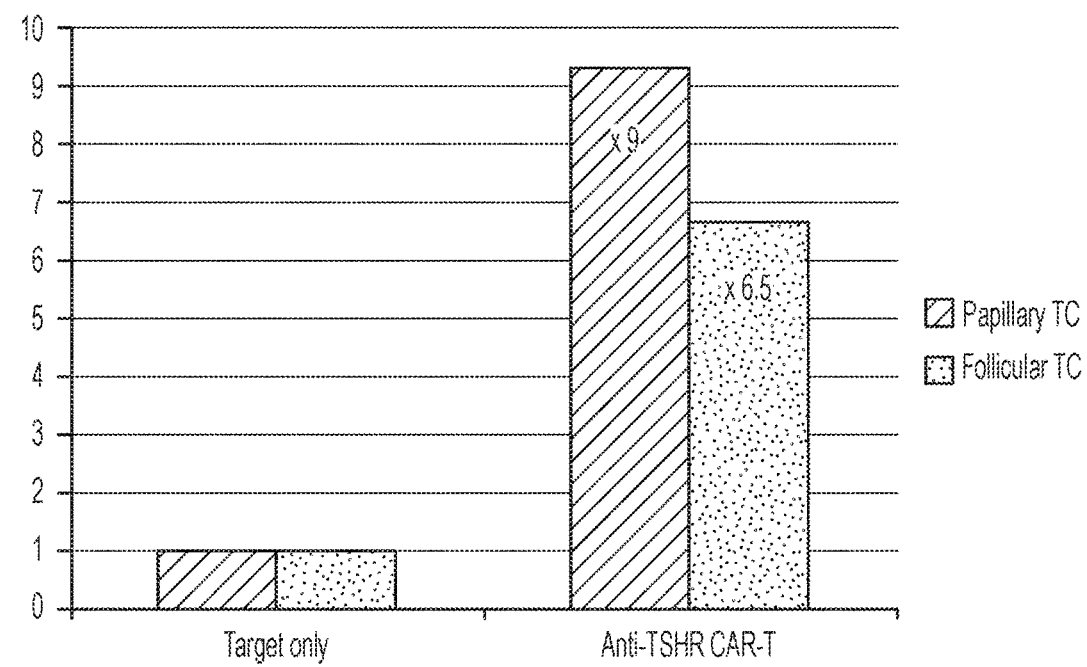
FIG. 7 shows caspase luminescence is elevated where tumor cells are treated with anti-TSHR-CAR-T.

To provide a more quantitative measure of cell death induced by CARTs, the level of caspase 3 and caspase 7, which play a critical role in the execution-phase of cell apoptosis, were analyzed. Caspase-Glo 3/7 Assay (Promega) was used to measure the level of caspase 3/7 after co-culturing with K-1 and FTC-133 cells. The amount of caspase 3/7 expression was compared between target cells only (thyroid cancer cells), target cells+peripheral blood (PB, including wild-type T cells without CARs), target cells+non-thyroid-specific CARTs (anti-CD19), and target cells+anti-TSHR CARTs. Using this caspase 3/7 assay, it was demonstrated that anti-TSHR CARTs significantly increased cell killing over peripheral blood cells and non-specific CART cells. Compared to PB, anti-TSHR CARTs increased caspase expression by 38.1% in K-1 cells and 94.2% in FTC-133, whereas the off target anti-CD19 CAR T cells had no effect on K-1 and only a modest effect on FTC-133 cells (FIG. 7).

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

What is claimed is:

1. A chimeric antigen receptor (CAR) comprising: an antigen binding domain a single-chain variable fragment (scFv) specific for thyroid specific hormone receptor (TSHR), wherein the scFv comprises the following complementarity determining regions (CDRs): NYWMN (SEQ ID NO: 11), RIDPSDSETHYNQNFKD (SEQ ID NO: 12), SGY, KSSQSLLDSDGKTYLN (SEQ ID NO: 14), LVSKVDS (SEQ ID NO: 15), and WQGTHSPLT (SEQ ID NO: 16); a transmembrane domain; a cytoplasmic domain containing one or more of a CD28 signaling domain, a CD 137 intracellular domain, a CD27 domain, a CD3zeta signal transduction domain; and a cytoplasmic domain that contains an inducible trigger of apoptosis.

2. The CAR of claim 1, wherein the transmembrane domain is a CD28 or CD8 transmembrane domain.

3. The CAR of claim 1, wherein the cytoplasmic domain contains two or more of a CD27 signaling domain, a CD137, and a CD3zeta signal transduction domain.

4. The CAR of claim 1, wherein the cytoplasmic domain contains a CD27 signaling domain, a CD137, and a CD3zeta signal transduction domain.

5. A nucleic acid comprising a sequence that encodes the CAR of claim 1.

6. An immune cell comprising a CAR of claim 1.

7. The immune cell of claim 6, wherein the immune cell is a T cell or NK cell.

8. The immune cell of claim 7, wherein the immune cell is a T cell.

9. A composition comprising a plurality of the immune cell of claim 6.

10. The composition of claim 9, further comprising a pharmaceutically acceptable carrier.

11. The CAR of claim 1, wherein the inducible trigger of apoptosis is iCasp9.

12. The composition of claim 9, wherein the inducible trigger of apoptosis is iCasp9.

* * * * *

UNITED STATES PATENT AND TRADEMARK OFFICE
CERTIFICATE OF CORRECTION

PATENT NO. : 11,634,498 B2
APPLICATION NO. : 16/097437
DATED : April 25, 2023
INVENTOR(S) : Scott A. Rivkees et al.

It is certified that error appears in the above-identified patent and that said Letters Patent is hereby corrected as shown below:

In the Claims

In Claim 1, Column 65, Line 55-56, the text "an antigen binding domain" should be removed Signed and Sealed this
Twenty-seventh Day of June, 2023

Katherine Kelly Vidal
*Director of the United States Patent and Trademark Office*